(12) United States Patent
Staub et al.

(10) Patent No.: US 11,197,954 B2
(45) Date of Patent: Dec. 14, 2021

(54) CANNULA INSERTION MECHANISM FOR A PATCH DEVICE

(71) Applicant: TecMed AG, Burgdorf (CH)

(72) Inventors: Seline Staub, Volketswil (CH); Ursina Streit, Schönbühl (CH)

(73) Assignee: TecMed AG, Burgdorf (CH)

( * ) Notice: Subject to any disclaimer, the term of this patent is extended or adjusted under 35 U.S.C. 154(b) by 335 days.

(21) Appl. No.: 16/516,051

(22) Filed: Jul. 18, 2019

(65) Prior Publication Data
US 2019/0336679 A1    Nov. 7, 2019

Related U.S. Application Data

(63) Continuation of application No. PCT/IB2018/050166, filed on Jan. 11, 2018.

(30) Foreign Application Priority Data

Jan. 19, 2017   (CH) ..................................... 00062/17
Feb. 23, 2017   (CH) ..................................... 00208/17

(51) Int. Cl.
*A61M 5/158*   (2006.01)
*A61M 5/142*   (2006.01)

(52) U.S. Cl.
CPC ........ *A61M 5/158* (2013.01); *A61M 5/14248* (2013.01); *A61M 2005/14252* (2013.01); *A61M 2005/1585* (2013.01)

(58) Field of Classification Search
CPC ...... A61M 2005/14284; A61M 5/3287; A61M 5/158; A61M 5/14248; A61M 2005/14252; A61M 2005/1585
See application file for complete search history.

(56) References Cited

U.S. PATENT DOCUMENTS 7,128,727 B2   10/2006  Flaherty et al.
7,909,791 B2 *  3/2011  Liniger ................. A61M 5/158
                                                         604/9

(Continued)

FOREIGN PATENT DOCUMENTS

CH        713377 A2    7/2018
CH        713378 A2    7/2018

(Continued)

OTHER PUBLICATIONS

PCT, "International Preliminary Report on Patentability", Application No. PCT/IB2018/050166, dated Jul. 23, 2019, 7 pages.

(Continued)

*Primary Examiner* — Theodore J Stigell
*Assistant Examiner* — Rachel T. Smith
(74) *Attorney, Agent, or Firm* — Dorsey & Whitney LLP

(57) ABSTRACT

A drive mechanism for an insertion mechanism for an administering device, having a base and a guide track. A slider of the drive mechanism provided on the base in a rotationally fixed manner can be slid along or in the guide track between end positions. A drive wheel is rotatably mounted on the base. A drive track is connected to the slider and has a plurality of drive sections, and an energy source, by means of which the drive wheel can be set into rotation. Upon rotation of the drive wheel, the slider moves along the guide track in the distal direction to a distal end of the guide track and slider is moved along or in the guide track in the proximal direction. The energy source can be coupled to the drive wheel by means of a one-piece or multi-piece transmission element and of an introduction wheel.

19 Claims, 14 Drawing Sheets

(56) References Cited

U.S. PATENT DOCUMENTS

| | | |
|---|---|---|
| 9,220,838 B2 | 12/2015 | Soma et al. |
| 2005/0222537 A1 | 10/2005 | Dinsmoor et al. |
| 2014/0142508 A1 | 5/2014 | Diianni et al. |
| 2015/0174317 A1 | 6/2015 | Momose |
| 2017/0165451 A1* | 6/2017 | Frey ..................... A61M 25/00 |
| 2020/0316314 A1 | 10/2020 | Buri et al. |

FOREIGN PATENT DOCUMENTS

| | | | | |
|---|---|---|---|---|
| CH | 713379 A2 | | 7/2018 | |
| CH | 713403 A2 | | 7/2018 | |
| EP | 2762183 A1 | | 8/2014 | |
| EP | 3501577 A1 | | 6/2019 | |
| GB | 2396298 A | * | 6/2004 | .......... A61M 5/2033 |
| WO | 9902208 A1 | | 1/1999 | |
| WO | 2012143434 A2 | | 10/2012 | |
| WO | 2013153041 A2 | | 10/2013 | |
| WO | 2016145094 A2 | | 9/2016 | |
| WO | 2019123074 A1 | | 6/2019 | |

OTHER PUBLICATIONS

PCT, "International Search Report and Written Opinion", Application No. PCT/IB2018/050166, dated Apr. 9, 2018, 17 pages.

International Preliminary Report on Patentability received for International Application No. PCT/IB2018/059688, dated Jun. 23, 2020, 12 page.

"International Preliminary Report on Patentability", Application No. PCT/IB2018/050166, dated Jul. 23, 2019, 7 pages.

"International Search Report and Written Opinion", Application No. PCT/IB2018/050166, dated Apr. 9, 2018, 17 pages.

* cited by examiner

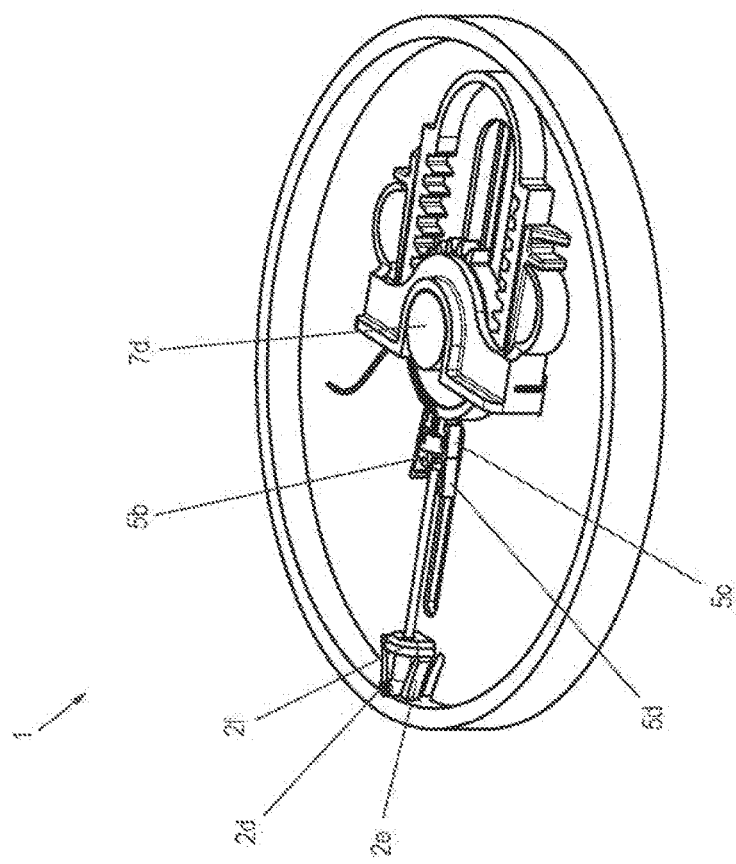
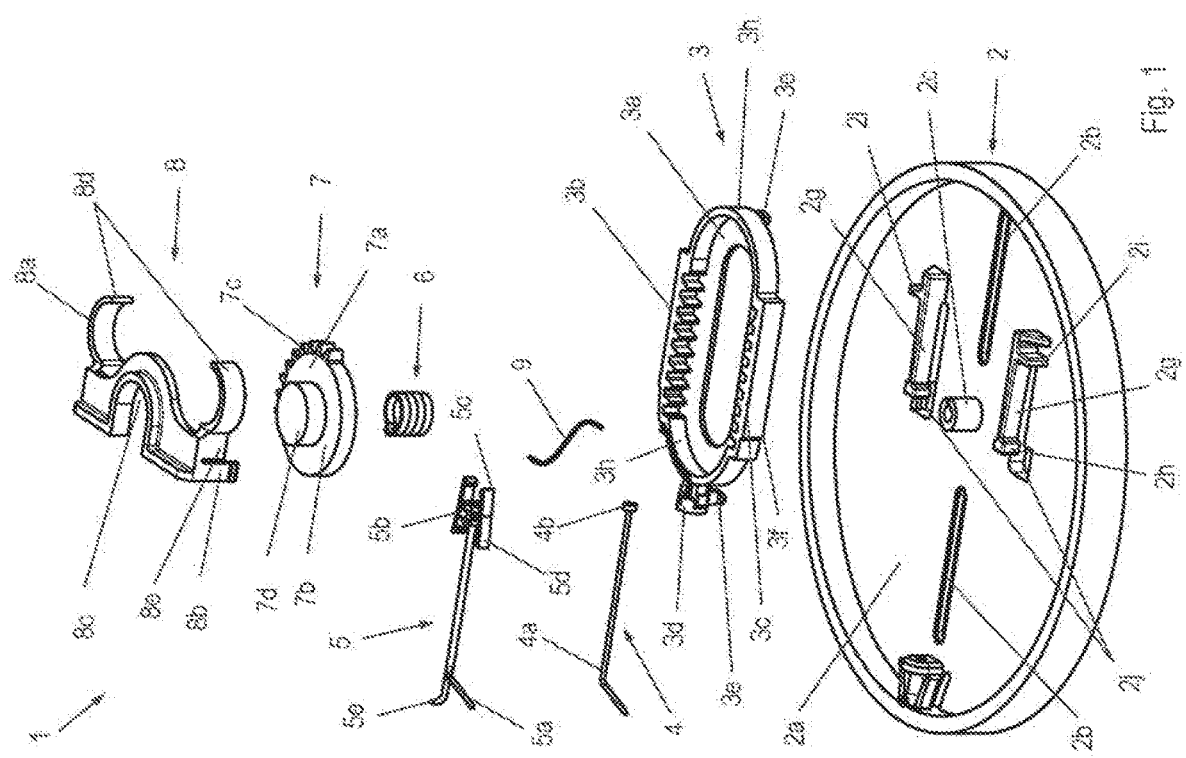

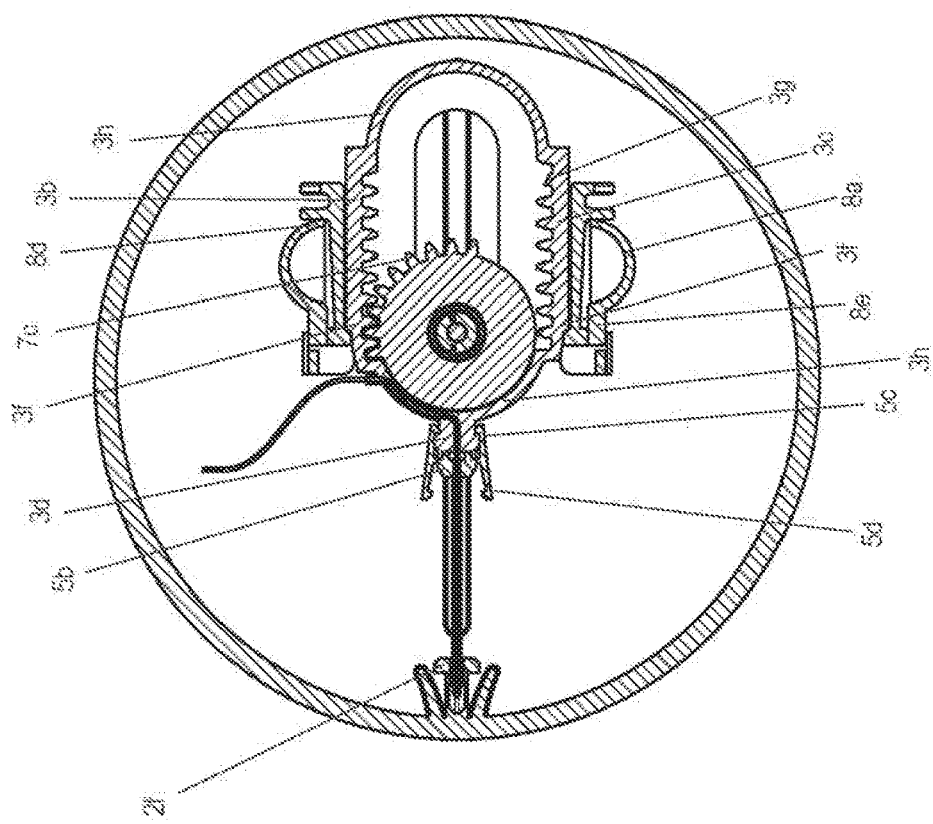

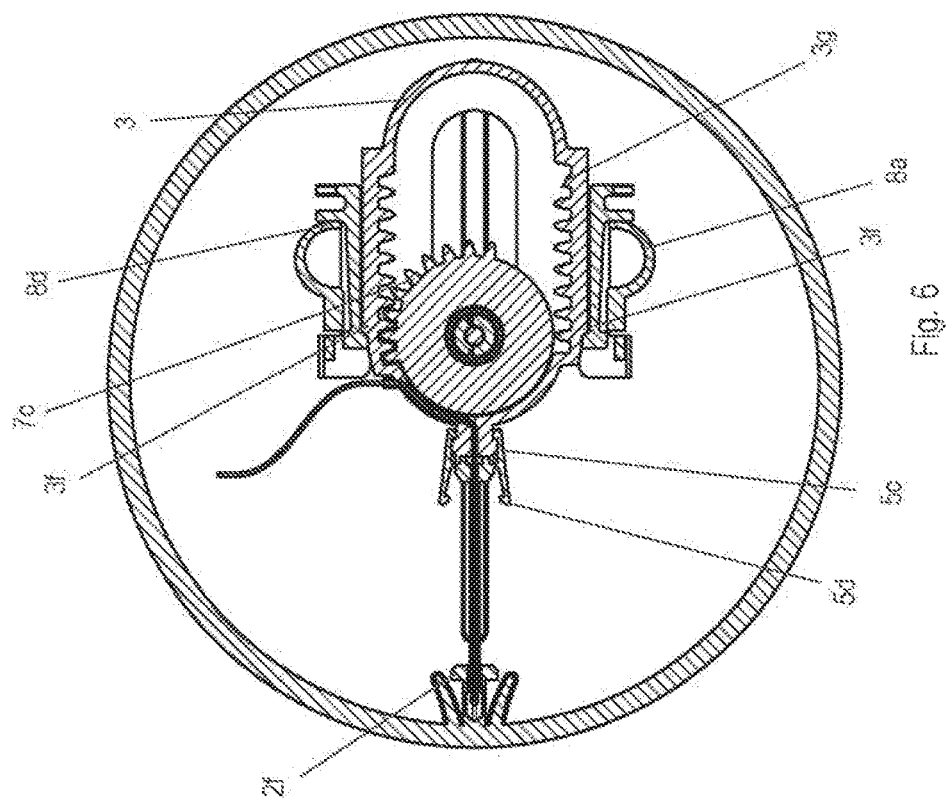
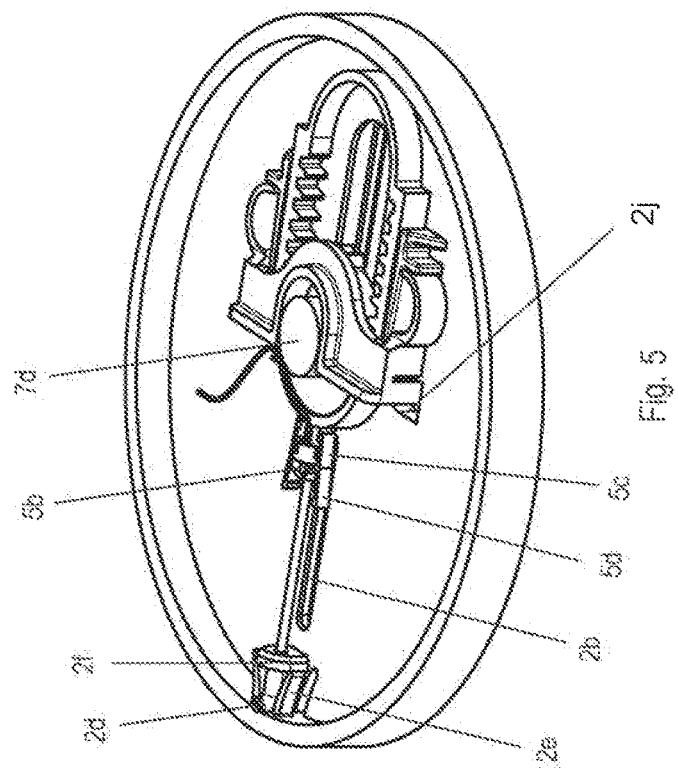

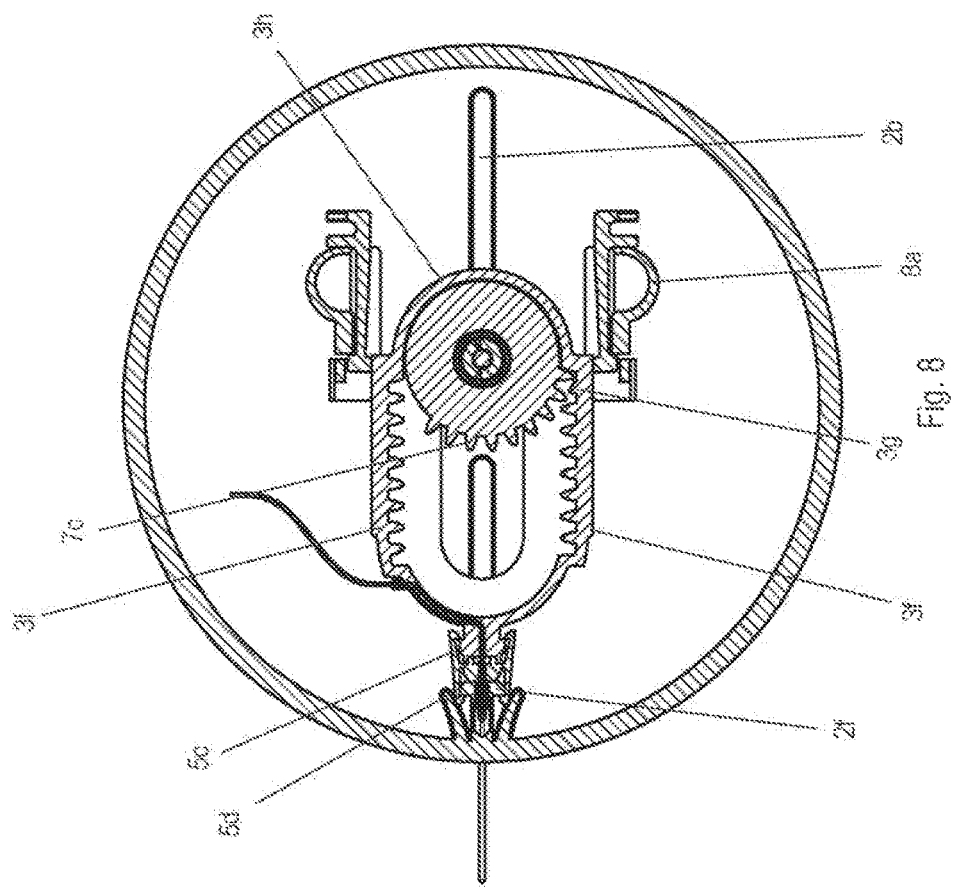
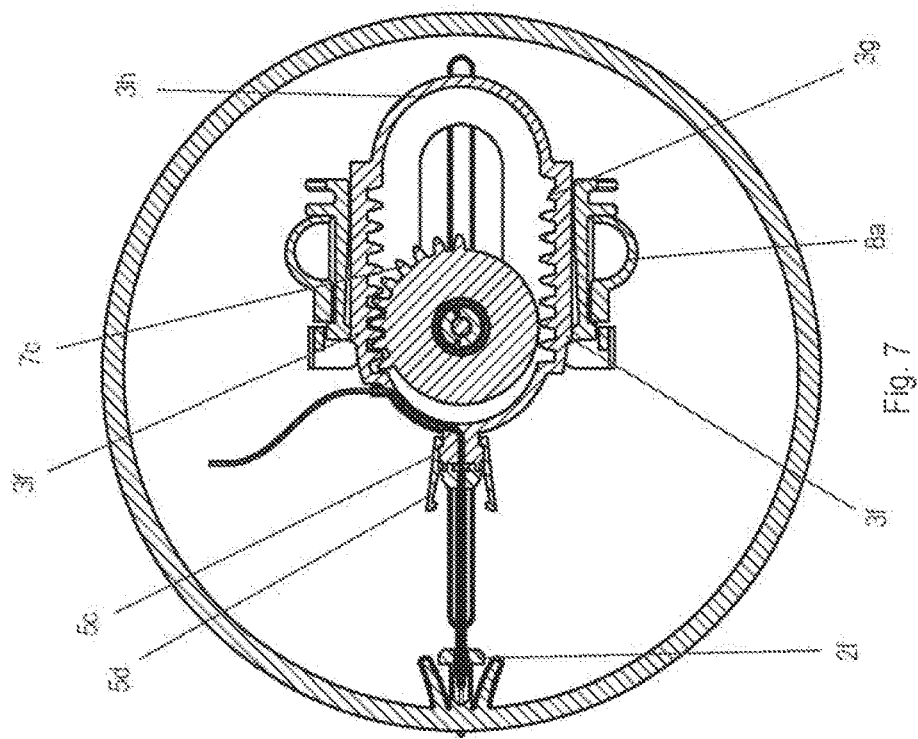

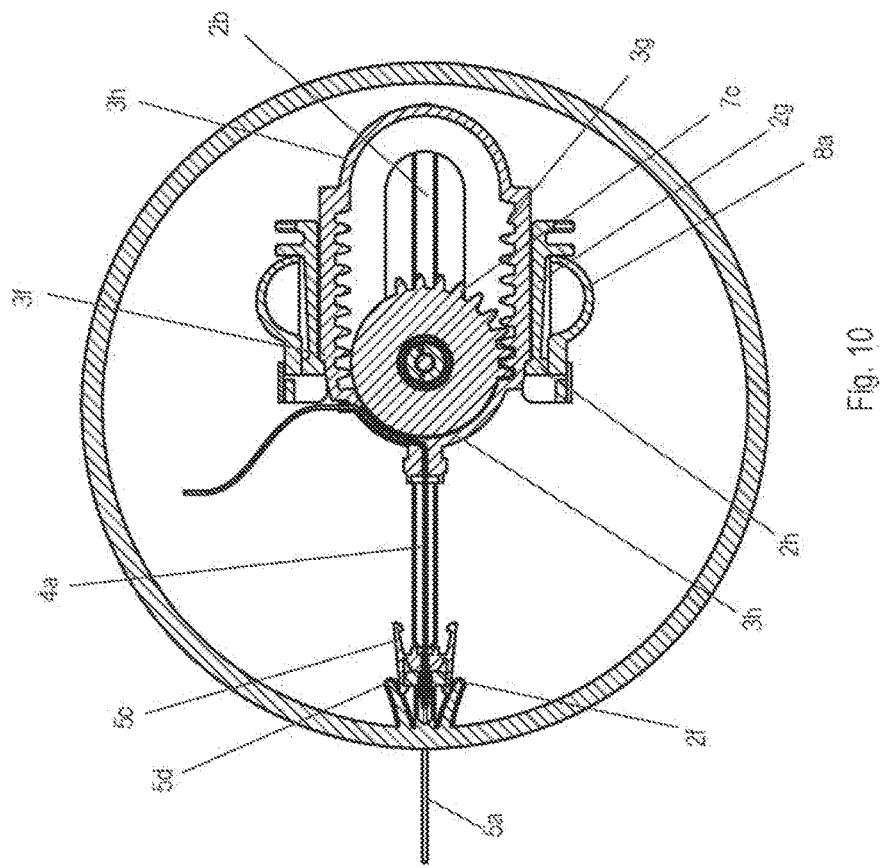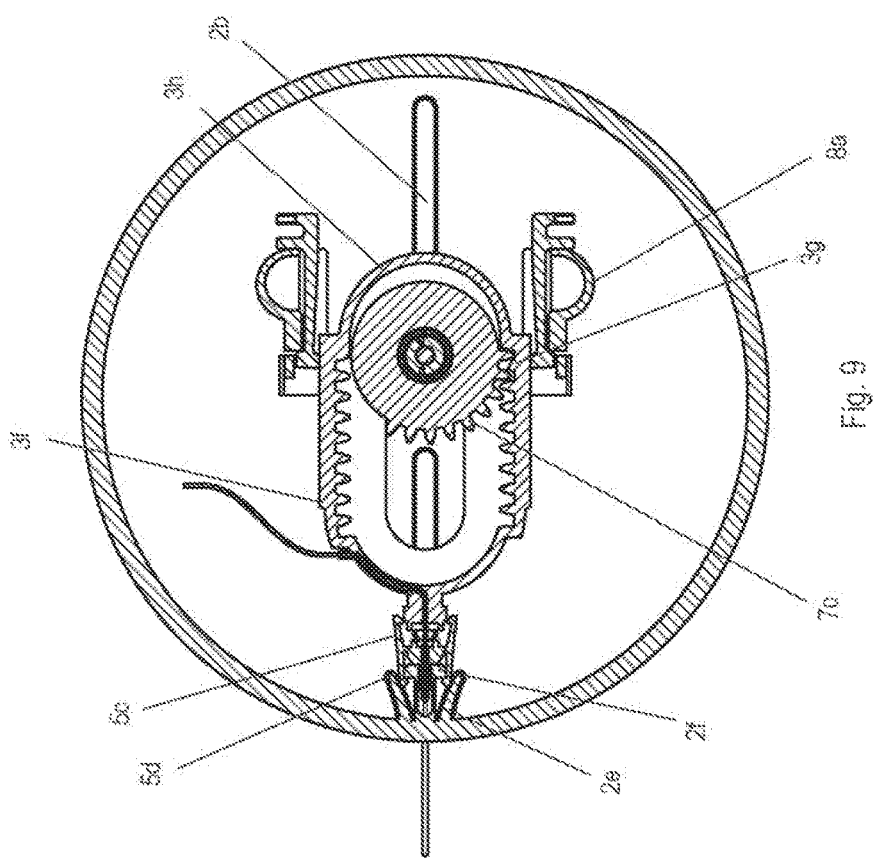

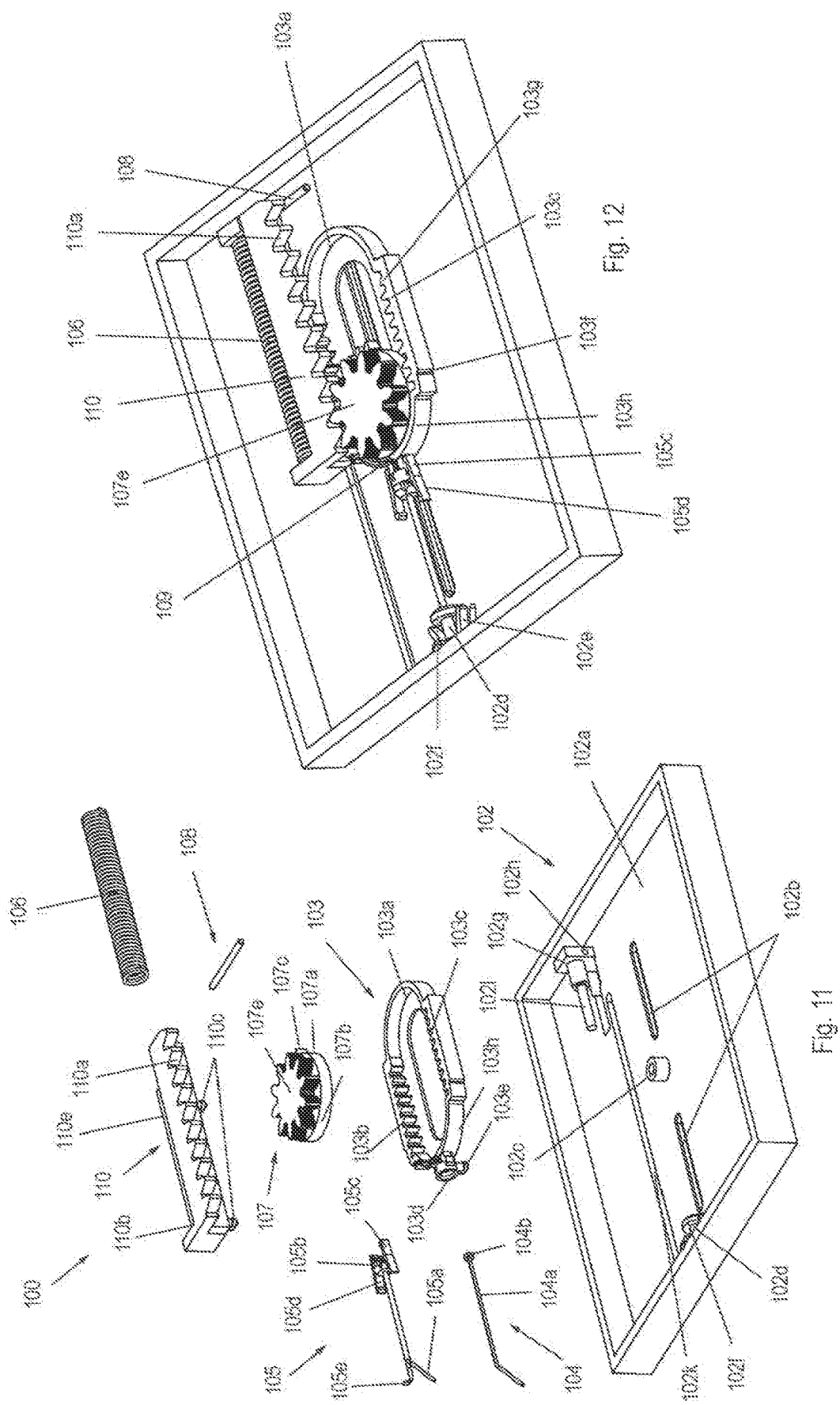

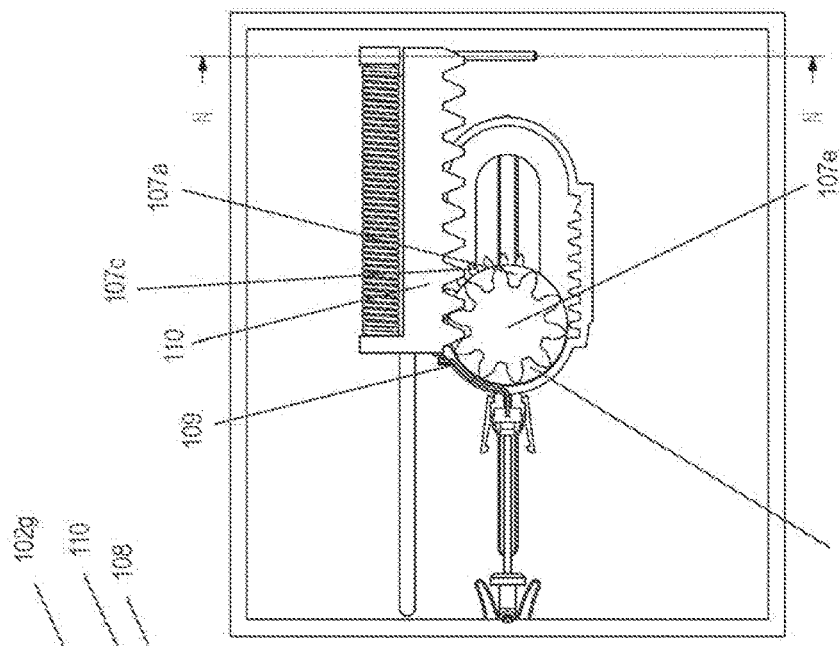
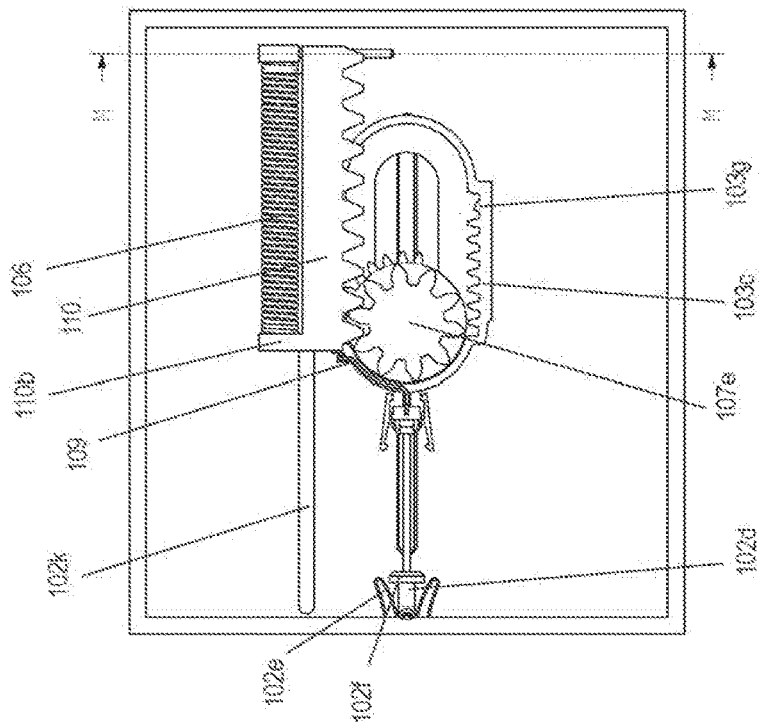

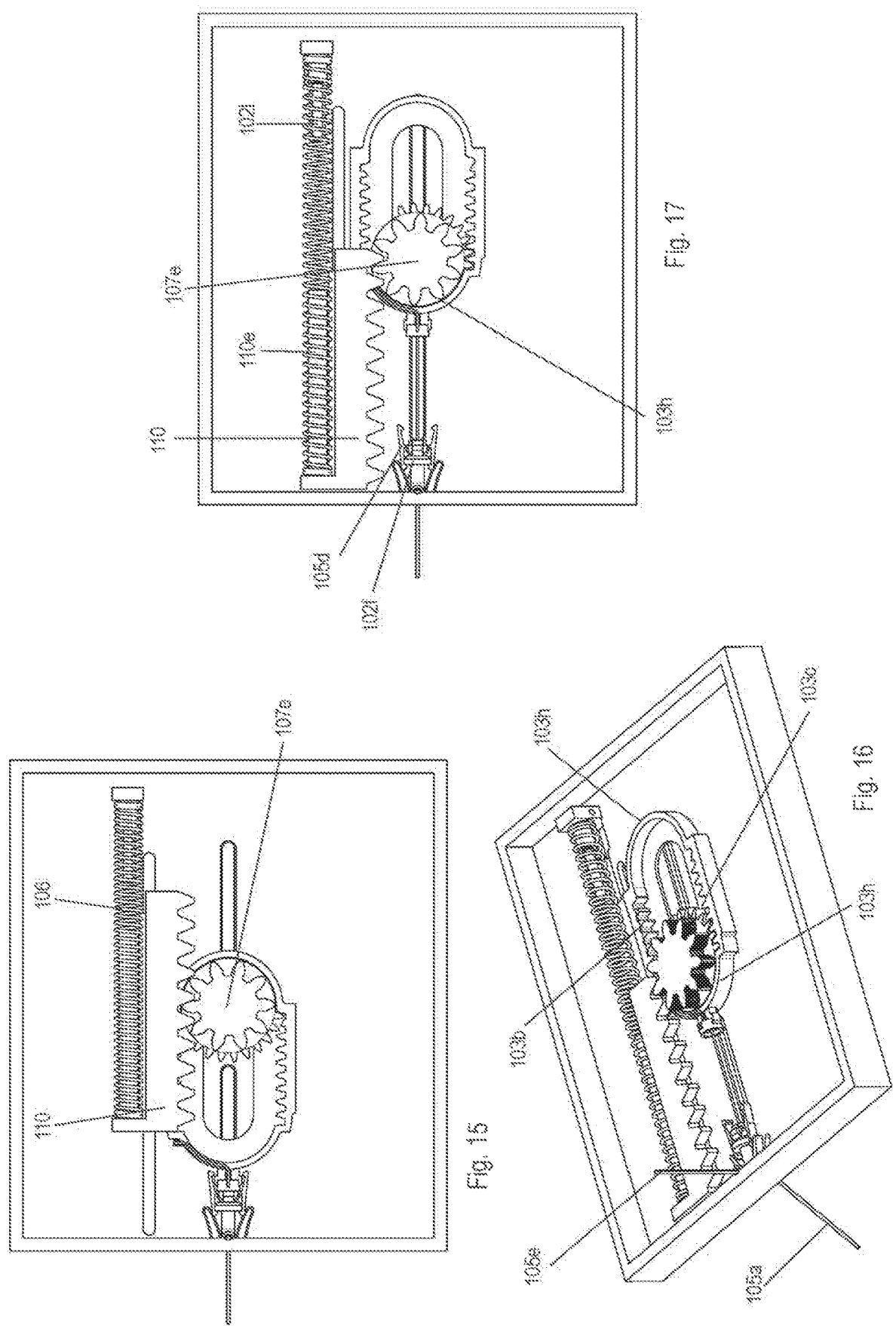

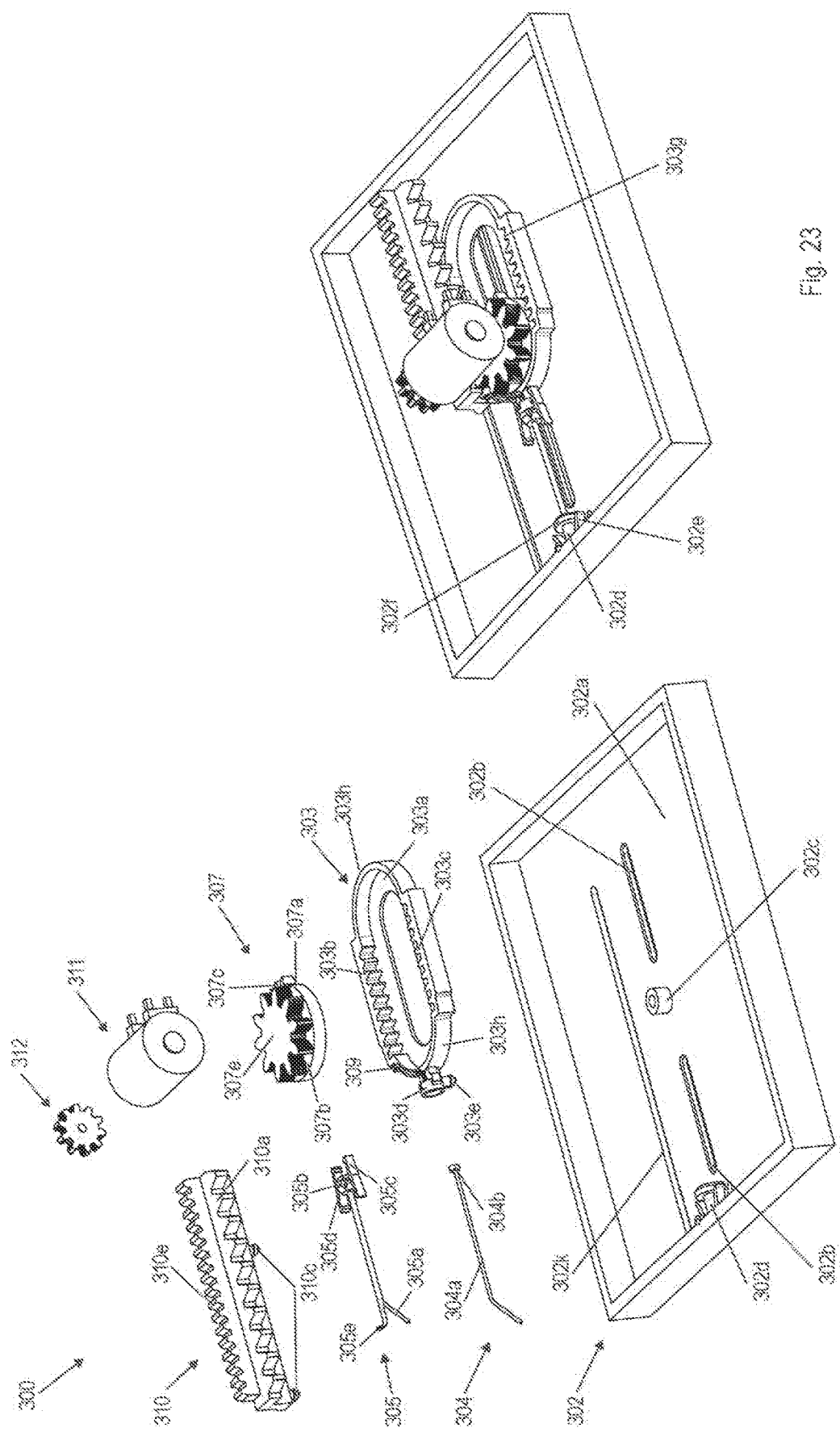

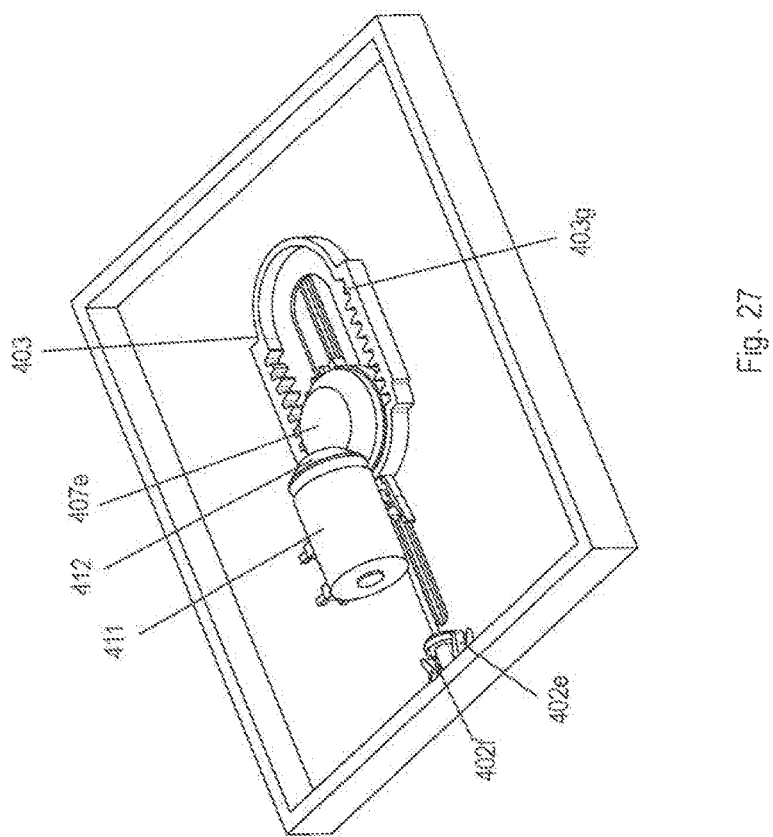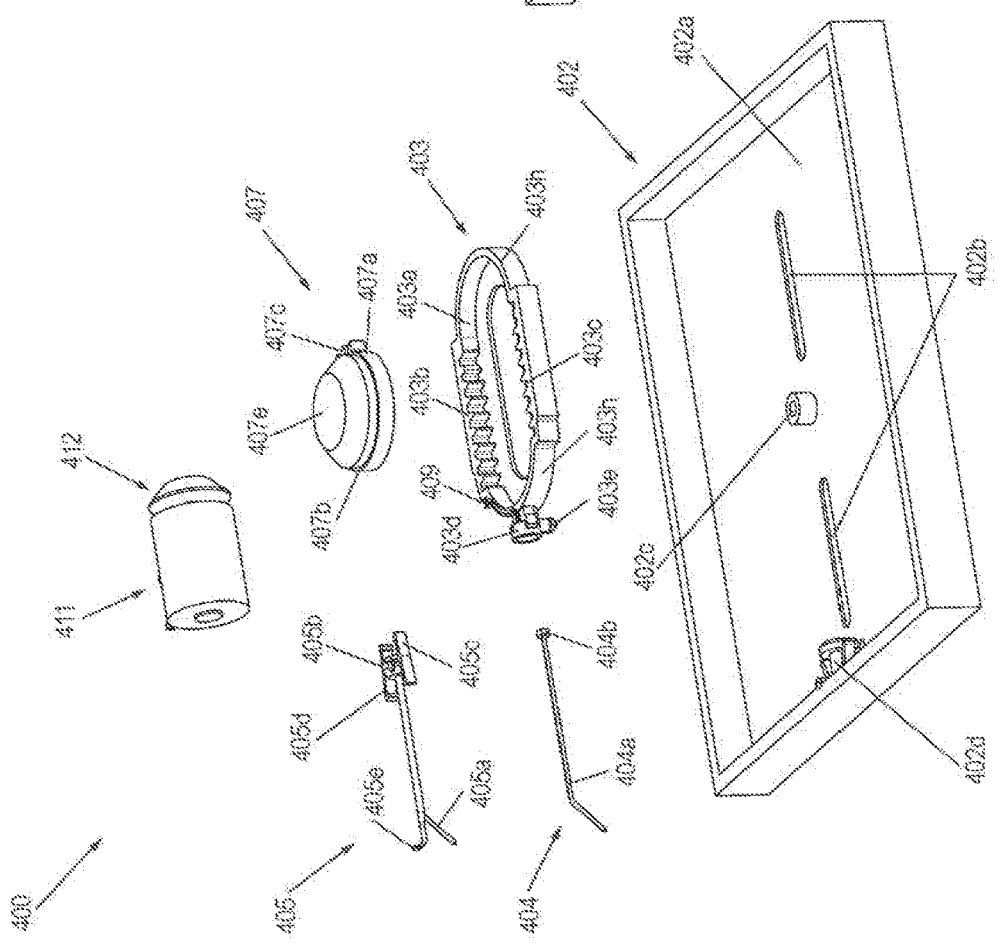

CANNULA INSERTION MECHANISM FOR A PATCH DEVICE

CROSS-REFERENCE TO RELATED APPLICATIONS

This application is a continuation of International Application No. PCT/IB2018/050166 filed Jan. 11, 2018, which claims priority to Swiss Application Nos. 00062/17, filed Jan. 19, 2017, and 00208/17, filed Feb. 23, 2017, the entire contents of all of which are incorporated by reference herein in their entirety.

FIELD OF THE INVENTION

The invention relates to injection and infusion devices, in particular injection and infusion devices which, for administering a substance, are attached, in particular glued, directly to the skin of the user, which are also known as patch devices. In particular, the invention relates to mechanisms for the insertion of cannulas, in particular so-called soft cannulas, which are produced, for example, from fluoropolymers (such as polytetrafluoroethylene) or substances having similar properties.

BACKGROUND

A dispensing device (also known as an administration device) for fluid products, in particular in an infusion pump or an injection device, in particular a patch infusion pump or patch injector, can in principle be suitable for administering a large variety of medications, provided that the medication has a consistency that can be discharged with the infusion pump or the injection device. However, the mentioned consistency, which is understood to mean the viscosity, for example, can make it necessary to optimize the construction of the injection device or of the infusion pump, in order to make administering the medication as pleasant as possible for the user. A possibility for such an optimization is the use of so-called patch devices (patch infusion pump, in particular in the treatment of diabetes with insulin, or patch injectors, in particular for administering antibody formulations having a high viscosity). The devices are glued directly to the body of the user by means of adhesive strips and thus no longer have to be manually held or accommodated in a holder, for example.

The term "medication" here comprises any free-flowing medicinal formulation that is suitable for controlled administration through a means such as, for example, a cannula or hollow needle, comprising, for example, a liquid, a solution, a gel or a fine suspension, which contains one or more medicinal active substances. A "medication" can be a composition with a single active ingredient or a premixed or co-formulated composition with several active ingredients from a single container. Medications include drugs such as peptides (for example, insulins, insulin containing medications, GLP-1-containing preparations as well as derived or analogous preparations), proteins and hormones, biologically obtained or biologically active ingredients, active ingredients based on hormones or genes, nutrient formulations, enzymes, and other substances either in solid (suspended) or fluid form, but also polysaccharides, vaccines, DNA or RNA or oligonucleotides, antibodies or parts of antibodies as well as suitable base, auxiliary and carrier substances.

SUMMARY OF THE INVENTION

Patch devices in the sense of the present invention, that is to say patch infusion pumps or patch injectors, commonly comprise so-called (cannula) insertion mechanisms which are used to introduce a cannula into tissue of the user. For administering the fluid medication, some of these patch devices use soft infusion cannulas that are made of plastic, in particular compatible fluoropolymers. This has the advantage that, when the surrounding tissue of the user is moved, the soft infusion cannula potentially causes less pain to the user than an infusion cannula made of a stiff material such as steel. Another advantage of the soft infusion cannulas is that no breaks can occur with soft cannulas. In order to be able to introduce soft infusion cannulas in the tissue in the first place, an insertion cannula (or an insertion needle) made of a stiff material such as steel is used. Before the introduction of the infusion cannula, this insertion cannula is introduced through the infusion cannula and protrudes past the open end of the infusion cannula. During the introduction, the insertion cannula together with the infusion cannula is stuck into the tissue. When the infusion cannula has reached its final position in the tissue, the infusion cannula is fixed in this position, and the insertion cannula is retracted from the tissue. Then, only the soft infusion cannula remains in the tissue.

In some insertion mechanisms, the inner lumen of the insertion cannula is part of the fluid path via which the fluid medication is administered. In this case, during the above-described retraction, the insertion cannula is not pulled completely out of the infusion cannula, so that the fluid medication to be administered is led from the insertion cannula into the infusion cannula and from there it reaches the tissue of the user via one or more openings of the infusion cannula.

From U.S. Pat. No. 7,128,727 B2, a patch infusion pump 10 with an insertion mechanism is known, by means of which a soft infusion cannula 38 is introduced into the tissue with the aid of an insertion cannula 62. For the insertion movement of the infusion cannula and the subsequent retraction of the insertion cannula, the mechanism described uses separate springs 70 and 82, respectively, that is to say at least one spring 70 that delivers the energy for the insertion movement and at least one spring 82 that delivers the energy for the retraction movement.

From US 2014142508 A1, a patch infusion pump 100 with insertion mechanism is known, by means of which a soft infusion cannula 176 is introduced with the aid of an insertion cannula 174 into the tissue. The drive of the insertion mechanism is here implemented with a torsion spring 181. Here, the drive spring 181 is connected to a slider 184 via an arm system 183a, 183b. The two partial arms 183a and 183b are connected to one another via an articulation, so that the two partial arms 183a, 183b can be turned relative to one another in a plane. The disclosed insertion mechanism enables the performance of the insertion movement and of the retraction movement with a spring 181.

An aim of the invention is to provide drives for alternative cannula insertion mechanisms and alternative cannula insertion mechanisms for administration devices, in particular patch devices such as patch infusion pumps or patch injectors, which can be produced cost effectively and at the same time have a high reliability.

The aim is achieved according to the invention by the claims, the description and the figures.

In the present description, the terms distal and proximal are used with respect to position and direction indications. Distal is understood in reference to the fluid path of the administration device toward the user (in the administration or dispensing direction) and proximally is accordingly understood to mean the opposite. Thus, for example, the movement of an infusion cannula that is introduced into the tissue of the user is a movement in distal direction, which is also referred to as insertion direction below. The retraction movement of an insertion cannula back into the housing of an administration device thus is a movement in the proximal direction.

An aspect of the invention comprises a cannula insertion mechanism for a patch device, in particular a patch infusion pump or a patch injector. In the following description, insertion mechanisms for patch infusion pumps are discussed in particular, which, however, can also be used in the same form for patch injectors or also in other administration devices without deviating from the invention.

In an aspect of the invention, the patch infusion pump comprises a housing. The housing can have a one-piece or a multi-piece configuration and comprises a so-called base, which represents the area of the housing arranged via bandage on the skin of the user. The base in turn can be of a multipart configuration and it can also comprise inserts such as in particular guide elements that are attached to the base during the mounting. Alternatively, the base can also be implemented as an insert for the housing.

In an aspect of the invention, the patch infusion pump comprises an insertion mechanism for placing a flexible or soft infusion cannula in the tissue of the user. The flexible or soft infusion cannula here is introduced with the aid of an insertion cannula into the tissue.

In an aspect of the invention, the insertion mechanism of the patch infusion pump comprises a gear that can be set in motion, in particular into rotation, by an energy source and that is mounted on the base in particular in a manner so it can be rotated but not shifted.

In an aspect of the invention, the insertion mechanism comprises a slider on which the insertion cannula is firmly arranged, wherein the slider is operatively coupled to the gear, so that a movement, in particular a rotation of the gear, can result in a movement of the slider and thus of the insertion cannula. In the starting state, the infusion cannula is pulled over the insertion cannula and said infusion cannula is positioned in the context of the insertion process in the tissue of the user with the aid of the insertion cannula. After the positioning, the insertion cannula is retracted through the infusion cannula out of the tissue, wherein the lumina of the two cannulas remain connected to one another, so that the medication can be led via the insertion cannula into the infusion cannula and subsequently into the tissue of the user.

In an aspect of the invention, the insertion mechanism of the patch infusion pump comprises a guide crank (advantageously with one or more partial cranks), along which the gear can be guided via toothings or pin arrangements, wherein a rotation of the gear can be converted via the guide along the toothings or pin arrangements into a translation of the gear shaft relative to the guide crank.

In an aspect of the invention, multiple toothings and pin arrangements are arranged along the guide crank in such a manner that the gear shaft can be moved in a temporally staggered manner in different directions relative to the guide crank.

In an aspect of the invention, the gear is occupied only partially with teeth on its periphery, wherein it can be subdivided into two sectors, into a first sector that is toothed and a second sector in which no teeth are present. In alternative configurations, the gear could also have more than two sectors, wherein toothed and untoothed sectors alternate.

In an aspect of the invention, the guide crank comprises a first toothed partial crank and a second toothed partial crank, wherein the first and the second partial cranks face one another (antiparallel or mirrored) and wherein the teeth of the first sector of the gear first rolls on the toothing of the first partial crank and, during further rotation of the gear, they roll in the same direction and then on the second partial crank, and wherein the teeth of the first sector are in engagement either with the first partial crank or the second partial crank, but not in engagement with the two at the same time. In this aspect of the invention, this sequential engagement of the teeth has the result that the guide crank moves relative to the gear shaft during the engagement of the teeth of the first sector into the toothing of the first partial crank along the first partial crank in a first direction and subsequently during the engagement of the teeth of the first sector into the toothing of the second partial crank along the second partial crank in a second direction that is opposite the first direction, resulting in a back and forth movement between guide crank and gear shaft. Optionally, between the engagement of the teeth of the first sector and the toothing of the first partial crank and the engagement of the teeth of the first sector in the toothing of the second partial crank, there can be a phase in which the teeth of the first sector are not in engagement with a toothing, so that the gear can rotate without the gear shaft moving relative to the guide crank.

In a partial aspect of the preceding aspect of the invention, the maximum angle that covers the first sector of the gear is defined as follows:

$$\text{maximum angle}_{\textit{first sector}} = 180° - ((\text{angle per tooth}) * \text{total number of the teeth in simultaneous engagement with a partial crank})$$

In another partial aspect of the preceding aspect of the invention, while the gear rolls on the first partial crank and the teeth of the first sector are in engagement with the toothing of the first partial crank, the relative movement between the first partial crank and the gear corresponds to the path of the insertion cannula during the introduction of the infusion cannula into the tissue.

In alternative configurations, the gear can be a friction wheel, wherein, instead of toothings or pin arrangements, the partial cranks then comprise corresponding friction surfaces along which the drive wheel can move in a non-positive connection.

In an aspect of the invention, the cannula insertion mechanism comprises an introduction wheel arranged in a rotationally fixed manner and coaxially on the gear, in particular an introduction gear. This introduction wheel is used to transfer movement energy from an energy source to the gear, wherein the gear is set in particular into rotation. The introduction wheel can be constructed and produced together with the wheel as one piece; alternatively, the gear and the introduction wheel can be produced as separate parts and be firmly connected together (i.e., in a manner so they cannot move with respect to one another) during the installation, for example, via a common axle or by joining techniques such as gluing or welding.

In an aspect of the invention, the cannula insertion mechanism comprises an elongated transmission element guided on the housing, in particular on the base, which can be brought in contact with the introduction wheel, in particular so that energy can be transmitted. By a relative rolling of the introduction wheel on the transmission element, the linear relative movement between introduction wheel and transmission element can be converted into a rotation of the introduction wheel and thus a rotation of the gear. The contact with transmission element can be a positive or non-positive connection. In a variant, the introduction wheel is mounted in a manner so it can be rotated but not shifted on the base, and the transmission element can be shifted in particular linearly with respect to the base and thus with respect to the introduction wheel. This results in a drive mechanism for the cannula insertion mechanism in which a linear movement is converted into a rotation. The transmission element can be shifted, for example, by a drive spring as a source of energy. The drive spring can be a compression spring that expands when energy is released. In a variant, the drive spring can be a tension spring that contracts when energy is released. In a configuration, for shifting the transmission element, a hydraulic or pneumatic drive (cylinder/piston) can be used. In an additional configuration, for shifting the transmission element, an electric drive mechanism can also be used, for example, an electric motor that is connected via a gear or a worm gear to the transmission element, a linear motor in particular with piezo oscillation drive mechanism, or a solenoid drive mechanism. The electric motor can be a DC motor or a step motor, wherein additional variants are familiar to the person skilled in the art. In an additional alternative, attracting or repelling magnets can also be used for the drive mechanism. The advantage of the described electric drives is that they can have a self-locking configuration, that is to say no separate devices are needed for holding the cannula insertion mechanism in the starting state or end state. This self-locking configuration can be implemented, for example, via the inner resistance (cogging torque) of an electric motor, when said electric motor is not switched on, for example, in the case of a DC motor with a permanent magnet. Alternatively, this self-locking can also be achieved by means of a worm gear that couples a motor and a transmission element.

In an aspect of the invention, the introduction wheel is configured as an introduction gear and the transmission element is configured as a toothed rod. In this aspect, the toothed rod is guided in a linear manner (linearly), and the introduction gear with the toothed rod is rotatably mounted on the base. The toothed rod has a toothing along a longitudinal dimension that can be brought in engagement with teeth of the introduction gear, wherein a movement of the toothed rod can be converted into a rotation of the introduction gear and the gear, wherein the toothed rod can be set in motion by energy from a spring or an electric drive mechanism.

In an aspect of the invention, the introduction wheel and thus also the gear are set into rotation by an electric drive mechanism, wherein the toothed rod is omitted, and wherein, in this aspect, the introduction wheel and the gear are advantageously mounted in a manner such that they can be rotated but not shifted on the base or the housing. Here, the introduction wheel can be constructed in particular as a bevel gear wheel, in particular as a bevel gear, in order to be able to configure the introduction of the energy efficiently and in a space saving manner. The introduction wheel can here be driven by an electric motor which, for example, via a transmission or an additional bevel gear wheel used as transmission element and arranged firmly on the axle driven by the motor, is connected to the introduction wheel, wherein, in this configuration, the additional bevel gear wheel performs the function of the transmission element.

In an aspect of the invention, the transmission element can be a chain, a string or a belt that couples the introduction wheel to the electric.

Additional aspects of the invention are reproduced below:

In an aspect, the invention comprises a cannula insertion mechanism for a patch device with:
   a housing comprising a base that can also be used as a base for the patch device and that can be attached directly or indirectly to the skin of the user,
   at least one guide track that is attached firmly to the housing and that defines at least a portion of an insertion path,
   a slider that is mounted such that it can be shifted in the at least one guide track in and opposite an insertion direction along the guide path,
   steel cannula that is firmly attached on the slider and that protrudes approximately parallel to the direction of the shifting of the slider,
   a drive spring, in particular a torsion spring, whose axle extends approximately perpendicularly to at least one guide track and that can be attached by a first end of the drive spring firmly to the base or the housing,
   a gear that can be attached firmly on a second end of the drive spring, wherein its rotation axis coincides with the axis of the drive spring,
   wherein the toothing of the gear comprises a first sector of the gear, and wherein a second sector of the gear has no toothing,
   a self-enclosed guide crank that is arranged firmly on the slider and that extends with a spacing with respect to the at least one guide track, wherein the distance results from the geometric dimensions of the slider, drive spring and gear, and
   wherein the guide crank comprises at least one partial crank that extends in the same direction with respect to the guide track,
   wherein the at least one partial crank in each case has at least one toothing or pin arrangement that can be brought in engagement, as a function of the rotational orientation of the gear, with the teeth of the first sector,
   wherein the gear can be set into rotation by the release of energy from the drive spring, and, as a result, the slider with the steel cannula can be set in motion along the at least one guide track by engagement of the teeth of the gear with the toothing or pin arrangement of the at least one partial crank.

In an aspect, the invention comprises a cannula insertion mechanism for a patch device with a cannula made of soft plastic, in particular PTFE, which is designed so it can be pulled over the steel cannula.

In an aspect, the invention comprises a cannula insertion mechanism for a patch device wherein the drive spring is a torsion spring and has a helical shape.

In an aspect, the invention comprises a cannula insertion mechanism for a patch device wherein the drive spring is a torsion spring that has the form of a spiral spring.

In an aspect, the invention comprises a cannula insertion mechanism for a patch device wherein the gear wheel comprises a second sector in which no toothing is present.

In an aspect, the invention comprises a cannula insertion mechanism for a patch device wherein the guide crank comprises two partial cranks with toothing, wherein the two partial cranks lie in the same plane and the toothings face one another with a spacing, and wherein the spacing of the two partial cranks with respect to one another is determined by the diameter of the gear without its teeth, in particular by the pitch circle diameter of the gear.

In an aspect, the invention comprises a cannula insertion mechanism for a patch device wherein the gear is arranged rotatably on the base so that, when energy is released from the drive spring, the gear can be set into rotation relative to the slider.

In an aspect, the invention comprises a drive mechanism for an insertion mechanism for an administration device, comprising
- a flat or curved base
- a guide track formed in or on the base, guide track which defines a proximal and a distal end and in between a straight line or a curve
- a slider that is provided in a rotationally fixed manner on the base and that can be moved along or in the guide track between a proximal slider end position and a distal slider end position, in particular back and forth,
- a drive wheel rotatably mounted on the base,
- a drive track that is connected to the slider and that comprises multiple drive sections, wherein a first drive section and a second drive section face one another and extend parallel with respect to the straight line or with respect to the curve of the guide track,
- an energy source by means of which the drive wheel can be set into rotation relative to the base and the slider,
- wherein the rotation of the drive wheel of the slides, starting in particular from the proximal slider end position, is shifted in the distal direction by a positive or non-positive connection engagement of the drive wheel in the first drive section along or in the guide track, until, at the distal end of the first drive section, the positive or non-positive connection engagement of the drive wheel switches from the first drive section to the second drive section by a continued rotation of the drive wheel, and the slider is consequently shifted along or in the guide track in the proximal direction, wherein the energy source can be coupled via a single-piece or a multi-piece transmission element and an introduction wheel with the drive wheel, wherein the introduction wheel is connected in a rotationally fixed manner to the drive wheel, and wherein the transmission element is arranged in a manner such that it can be shifted or rotated with respect to the base.

In an aspect, the invention comprises a drive mechanism for an insertion mechanism for an administration device according to the preceding aspect, wherein the transmission element is a toothed rod with at least one toothing and is arranged in a manner such that it can be shifted on the base, and wherein the introduction wheel is a gear whose teeth can be brought into engagement with a toothing of the toothed rod.

In an aspect, the invention comprises a drive mechanism for an insertion mechanism for an administration device according to the preceding aspect, wherein the base furthermore comprises a linear toothed rod guide, in particular in the form of a groove, and wherein the toothed rod comprises at least one guide element, in particular at least two cams, via which the toothed rod is connected to the base, and wherein the toothed rod can be shifted along the toothed rod guide.

In an aspect, the invention comprises a drive mechanism for an insertion mechanism for a drive device according to the preceding aspect, wherein the energy source is a tension or compression spring, wherein an end of the tension or compression spring is arranged firmly with respect to the base and a second end is arranged firmly with respect to the toothed rod, and wherein the tension or compression spring for driving the drive mechanism for the insertion mechanism of the administration device is pretensioned or can be pretensioned, and wherein, by a release of the pretensioned tension or compression spring, a force acts on the toothed rod, setting said toothed rod in motion along the toothed rod guide and wherein, as a result, the introduction wheel and drive wheel are set into rotation.

In an aspect, the invention comprises a drive mechanism for an insertion mechanism for an administration device according to a preceding aspect, wherein the drive mechanism moreover comprises a release device, wherein the release device comprises at least the following elements, a holding element firmly arranged on the base, an additional holding element firmly arranged on the toothed rod, and a connecting element by means of which the holding element and the additional holding element can be detachably connected to one another so that, when the holding element and the additional holding element are connected to one another via the connecting element, the toothed rod is firmly held or fixed relative to the base.

In an aspect, the invention comprises a drive mechanism for an insertion mechanism for an administration device according to the preceding aspect, wherein the holding element and the additional holding element are bores, and the connecting element is configured as a pin or splint that can be introduced into the bores, and, as a result, the toothed rod can be fixed to the base.

In an aspect, the invention comprises a drive mechanism for an insertion mechanism for an administration device, wherein the toothed rod comprises a first and a second toothing, wherein the first toothing can be brought into engagement with the introduction wheel configured as a gear, and wherein the energy source can be coupled via the second toothing to the toothed rod.

In an aspect, the invention comprises a drive mechanism for an insertion mechanism for an administration device, wherein the energy source is an electric motor with an electric motor drive axle that can be set into rotation by the electric motor directly or via a transmission, and wherein, on the electric motor drive axle, a gear is arranged coaxially and firmly, which can be brought in engagement with the second toothing of the toothed rod.

In an aspect, the invention comprises a drive mechanism for an insertion mechanism for an administration device, wherein the introduction wheel is implemented as a first bevel gear wheel, in particular as a bevel gear, and the transmission element is also implemented as a second bevel gear wheel, in particular as a bevel gear, wherein the first bevel gear wheel and the second bevel gear wheel are in engagement with one another, so that a rotation of the second bevel gear wheel brings about a rotation of the first bevel gear wheel, and wherein the rotation axes of the first and of the second bevel gear wheel are at an angle of approximately 90° with respect to one another.

In an aspect, the invention comprises a drive mechanism for an insertion mechanism for an administration device, wherein the second bevel gear wheel can be set into rotation by an electric drive or a spring.

In an aspect, the invention comprises a drive mechanism for an insertion mechanism for an administration device, wherein, on the slider, a feed line with a lumen is arranged and/or guided in or on the slider, through which feed line a substance to be administered, in particular a fluid medication, can be led.

In an aspect, the invention comprises a drive mechanism for an insertion mechanism for an administration device, wherein, on the distal end of the slider, a cannula bridge is arranged on which the feed line ends, and a proximal end of an insertion cannula with a lumen is arranged, wherein the lumen of the feed line and the lumen of the insertion cannula are connected to one another, so that the substance to be administered can be led from the feed line into the insertion cannula, and wherein the insertion cannula also undergoes a shifting of the slider in distal as well as in proximal direction.

An aspect of the invention comprises a cannula insertion mechanism for a patch device, comprising a drive as described above, an infusion cannula with a distal and a proximal end, through which the insertion cannula can be led, wherein, on the proximal end of the infusion cannula, a cannula carrier is firmly arranged, wherein on the cannula carrier a connection means, in particular one or more snap-in arms, is arranged, via which the cannula carrier can be detachably connected to the cannula bridge when the insertion cannula is led through the infusion cannula until the cannula carrier is in contact with the cannula bridge.

An aspect of the invention comprises a patch device, in particular a patch pump or a patch injection device, with a cannula insertion mechanism according to the preceding aspect.

In another aspect, the invention comprises a cannula insertion mechanism for a patch device, wherein, in the event of the rotation of the gear, the teeth of the first sector of the gear in a first phase come into an engagement with the toothing of the first partial crank, wherein, via the arrangement of the first partial crank on the slider, the slider is moved along the guide track in the insertion direction, and wherein the teeth of the first sector of the gear in a second phase come into engagement with the toothing of the second partial crank, whereby, via the arrangement of the first partial crank on the slider, the slider is moved along the guide track opposite the insertion direction.

In an aspect, the invention comprises a cannula insertion mechanism for a patch device, wherein the first sector of the gear with its teeth defines a pitch circle diameter, wherein the curvature resulting from the sector angle of the first sector and the pitch circle diameter determines the insertion path of the cannula insertion.

BRIEF DESCRIPTION OF THE DRAWINGS

FIG. 1: Exploded representation of the insertion mechanism of a patch infusion pump 1 which is the basis of the invention.

FIG. 2: View of the parts of the patch infusion pump shown in FIG. 1 in assembled state (starting state).

FIG. 3a: Vertical partial section through the arrangement from FIG. 2.

FIG. 3b: Detail from FIG. 3a.

FIG. 4: Horizontal section through the arrangement from FIG. 2 in the starting state.

FIG. 5: View of the insertion mechanism of the patch infusion pump from FIG. 2 immediately after release of the insertion mechanism.

FIG. 6: Horizontal section through the arrangement from FIG. 2 immediately after release of the insertion mechanism.

FIG. 7: Horizontal section through the arrangement from FIG. 2 during the insertion movement.

FIG. 8: Horizontal section through the arrangement from FIG. 2 after completed insertion, before the retraction of the insertion cannula 4a.

FIG. 9: Horizontal section through the arrangement from FIG. 2 during the retraction of the insertion cannula 4a.

FIG. 10: Horizontal section through the arrangement from FIG. 2 after the completed retraction of the insertion cannula 4a.

FIG. 11: Exploded representation of an inventive cannula insertion mechanism for the patch infusion pump 100.

FIG. 12: View of the parts of the patch infusion pump shown in FIG. 11 in assembled state (starting state).

FIG. 13a: View onto the arrangement of the cannula insertion mechanism from FIG. 12 in the starting state.

FIG. 13b: Vertical section of the arrangement from FIG. 13a in the area of the triggering mechanism.

FIG. 14a: View onto the arrangement of the cannula insertion mechanism from FIG. 12 immediately after triggering.

FIG. 14b: Vertical section of the arrangement from FIG. 14a in the area of the triggering mechanism.

FIG. 15: View onto the arrangement of the cannula insertion mechanism from FIG. 12 after completed insertion but before the retraction of the insertion cannula 104a.

FIG. 16: View of the arrangement of the cannula insertion mechanism from FIG. 12 after completed retraction of the insertion cannula 104a (final state).

FIG. 17: View of the arrangement of the cannula insertion mechanism from FIG. 12 after completed retraction of the insertion cannula 104a.

FIG. 20: View onto the arrangement of the cannula insertion mechanism from FIG. 19 after completed insertion but before the retraction of the insertion cannula 204a.

FIG. 22: Exploded representation of an inventive cannula insertion mechanism for the patch infusion pump 300.

FIG. 23: View of the parts of the patch infusion pump 300 shown in FIG. 22 in assembled state (starting state).

FIG. 24: View onto the arrangement of the cannula insertion mechanism from FIG. 23 after completed insertion but before the retraction of the insertion cannula 304a.

FIG. 26: Exploded representation of an inventive cannula insertion mechanism for the patch infusion pump 400.

FIG. 27: View of the parts of the patch infusion pump 400 shown in FIG. 26 in assembled state (starting state).

FIG. 28: View onto the arrangement of the cannula insertion mechanism from FIG. 27 after completed insertion but before the retraction of the insertion cannula 404a.

DETAILED DESCRIPTION

Figure 19:
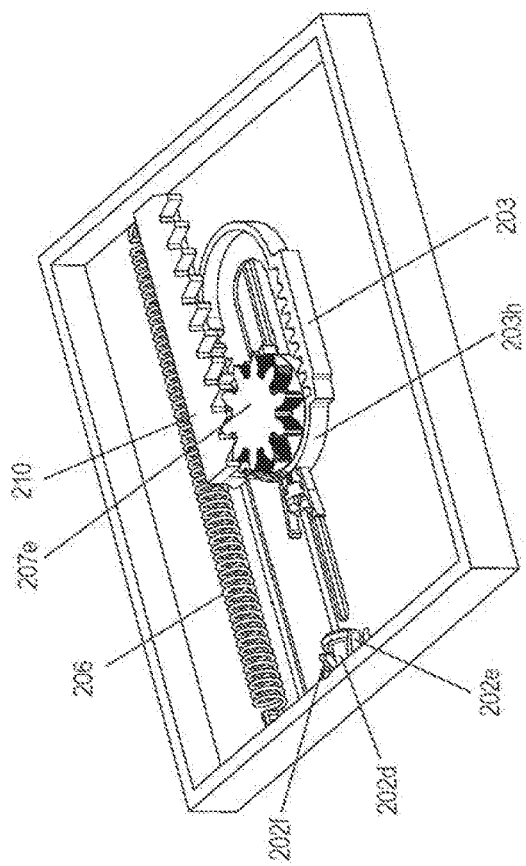
FIG. 19: View of the parts of the patch infusion pump 200 shown in FIG. 18 in assembled state (starting state).

The following figure descriptions and figures show and describe different possible embodiments and configurations of the invention. They do not provide a comprehensive listing of the possible embodiments of the invention, but only examples. From the description and representation, the person skilled in the art may become aware of other embodiments of the invention without in the process leaving the scope of the invention. In addition, by combining parts of different embodiments and configurations, the person skilled in the art can arrive at other embodiment variants, embodiment developments that are obvious to him, without leaving the scope of the invention. Such embodiment variants which are not shown here are explicitly made part of this document.

The following representations and embodiments do not show nor describe in each case entire administration devices such as patch infusion pumps or patch injection devices but, for the sake of clarity, only the parts that could be important to the invention.

FIGS. 1 to 10 show the basic cannula insertion mechanism of a patch infusion pump 1 that represents the basis of the embodiments according to the invention. The cannula insertion mechanism represented in FIGS. 1 to 10 has already been described in detail in the Swiss Patent Application No. 00062/17, which is herein incorporated by reference in its entirety.

FIG. 1 shows an exploded representation of the basic cannula insertion mechanism. FIG. 2 shows a view of the basic insertion mechanism in the starting state. FIG. 3a shows a vertical section through the basic cannula insertion mechanism in the starting state. FIG. 3b shows a detail from FIG. 3a. FIG. 4 shows a horizontal section through the cannula insertion mechanism in the starting state. FIGS. 5 and 6 show the cannula insertion mechanism immediately after triggering the mechanism in two different views. FIGS. 7 to 10 then show horizontal sections through the cannula insertion mechanism in the additional stages of the insertion process, wherein FIG. 10 represents the final state.

The patch infusion pump 1 comprises a housing 2 of which, in FIGS. 1 to 10, one can see primarily the base 2a, which in turn can be configured as a housing part or as a housing insert. The housing 2 is glued in the area of the base 2a to the skin of the user by means of adhesive tape.

The guide tracks 2b, which are configured as grooves, are arranged on the base 2a. Moreover, on the base, the spring holder 2c, the cannula guide 2d, the release arms 2g and the guides 2j implemented as openings in the base 2a are arranged. The basic cannula insertion mechanism moreover comprises a slider 3, which is guided with the aid of the guide elements 3e such that it can be shifted in the guide tracks 2b on the base. The slider moreover comprises the channel bridge 3d (also referred to as cannula bridge) on which the insertion cannula 4a is firmly arranged with its insertion cannula carrier 4b (see in particular FIG. 4). The insertion cannula is configured to be open at its two ends, so that the fluid can be led through the insertion cannula 4a. Also firmly connected to the cannula bridge 3d is the feed line 9, which is in fluid connection with the insertion cannula 4a and through which fluid can be led, for example, from a reservoir into the insertion cannula 4a. As can be seen in FIG. 4, the feed line 9 extends partially on the slider 3. As shown in FIGS. 1 to 10, the slider 3 has roughly the form of an oval. The oval has the function of a guide crank 3a, which consists of the first partial crank 3b, the second partial crank 3c and the two arcs 3h that connect the first partial crank 3b to the second partial crank 3c. The interior of the oval is open. The first partial crank 3b and the second partial crank 3c have toothings that face one another.

On the spring holder 2c, an end of the drive spring 6, in the case shown a helicoidal torsion spring, is firmly arranged; the spring 6 is here arranged coaxially with respect to the spring holder 2c and is also mounted by the spring holder. The second end of the spring is firmly connected to the gear 7, wherein the gear 7 is rotatably mounted with respect to the spring holder 2c on said spring holder and wherein the spring 6 is arranged between the spring holder 2c and the gear 7. The gear shaft 7d reaches through the oval of the slider 3. The gear 7 has a first sector 7a that has a toothing with teeth 7c. Moreover, the gear 7 comprises a second sector 7b without toothing. The two sectors 7a and 7b are mounted by the mentioned oval, wherein, when the gear 7 is rotated relative to the base 2a and the slider 3, the toothing of the first sector 7a can alternatively come in engagement with the toothings of the first partial crank 3b and the second partial crank.

The basic insertion mechanism comprises a cannula assembly 5, which comprises a cannula carrier 5b. The infusion cannula 5a is firmly anchored on the cannula carrier 5b. In the starting state, the insertion cannula 4a extends through the cannula carrier 5b and the lumen of the infusion cannula 5a, wherein the distal tip of the insertion cannula 4a protrudes from the distal end of the infusion cannula 5a. When the infusion cannula 5a is introduced into the tissue of the user, the insertion cannula 4a is pulled back through the infusion cannula 5a (out of the tissue), wherein, after completed retraction, the insertion cannula 4a still protrudes into the infusion cannula 5a and thus establishes the fluid connection between feed line 9 and infusion cannula 5a, so that the substance to be administered can be supplied to the user. The infusion cannula 5a is mounted together with the cannula carrier 5b movably on the insertion cannula 4a, wherein, in the starting state, cannula carrier 5b and the cannula bridge 3d are firmly but detachably connected to one another via the snap-in arms 5c.

FIGS. 3a and 3b show partial vertical sections through the patch infusion pump 1, wherein FIG. 3b shows details of the cannula guide 2d. In the insertion process, the slider 3 moves relative to the base. In many applications, the movement of the slider and thus of the insertion cannula 4a and also of the infusion cannula (during pricking) is approximately parallel to the skin surface of the user. For the insertion cannula 4a and the infusion cannula 5a to be guided with the correct angle into the tissue, the cannula guide 2d guides the insertion cannula 4a and the infusion cannula 5a in the direction of the tissue, which is shown in FIG. 3b. In optional configurations of the patch infusion pump 1, the cannula assembly 5 comprises a guide tube 5e, the task of which is to mechanically stabilize the cannula assembly 5 during the movement in the distal direction (see FIGS. 3a and 3b). The guide tube 5e encloses the infusion cannula 5a and is arranged with one end firmly on the cannula carrier 5b. Here, the guide tube 5e has a longitudinal slot on its side facing the base 2a. If the cannula assembly 5 is shifted in the distal direction, the guide tube 5e is opened along the slot in the area of the channel guide 2d and separated from the infusion cannula 5a and the insertion cannula 4a and not led through the base 2a in the direction of the tissue—in the present example away from the base 2a.

As already mentioned, the gear 7 is rotatably mounted on the spring holder 2c. Between the gear 7 and the spring holder 2c, the drive spring 6 is arranged, which is implemented as a helicoidal torsion spring. Here, it should be mentioned again that the drive spring could also have other forms, in particular, for example, the spring with the spring holder could be configured to be integrated as a torsion rod that would be firmly connected on one end to the gear 7. Back to the embodiment shown: one end of the drive spring 6 is firmly connected to the spring holder 2c, and the other end is firmly connected to the gear 7. Energy stored in the spring 6 can then be converted into a rotation of the gear 7 relative to the base 2a. As mentioned, the gear 7 is subdivided into a first sector 7a with teeth 7c and a second sector 7b without teeth. As mentioned, the guide crank 3a is arranged firmly on the slider 3 and comprises the first partial crank 3b and a second partial crank 3c.

In the starting state, the spring 6 is pretensioned so that a torque acts on the gear 7, which is transmitted via the teeth 7c to the first partial crank 3b on the slider 3. Subsequently, the slider 3 pushes in the distal direction. However, in the starting state, this movement is blocked, as can be seen in FIG. 4, for example. For this purpose, on the base 2a, release arms 2g are arranged, which have a free end with tooth 2h. In each case, in the starting state, a tooth 2h is in engagement with a tooth 3f of the slider 3 (in the variant shown, the basic insertion mechanism in each case has such a tooth 3f on the two sides of the slider 3). In order to prevent an outward flexion of the free end 2h of the release arm 2g in the starting state, the insertion mechanism of the patch infusion pump 1 moreover comprises a release clamp 8.

The release clamp 8 is connected to the base 2a via the guide arms 8b, which are mounted in such a manner that they can be shifted in the guides 2j. The release clamp moreover comprises the spring elements 8a, the free ends 8d of which are in contact with the recesses 2i of the release arms 2g and thus resiliently push the release clamp in the distal direction. The bay 8c of the release clamp 8 here mounts the gear axle 7d and also pushes the gear in the distal direction (see FIG. 2, for example).

As mentioned, FIG. 4 shows a horizontal section through the insertion mechanism in the starting state. Here, it becomes clear how the blocking zones 8e of the release clamp 8 prevent a deflection of the free ends of the release arms 2g. The insertion mechanism can then be released by a movement of the release clamp in the proximal direction opposite the spring force induced by the spring elements 8a. Due to the shifting of the release clamp 8 in the proximal direction, the blocking zones 8e are also shifted in the proximal direction.

In FIGS. 5 and 6, the insertion mechanism is shown with release clamp 8 actuated. In this state, the free ends 2h of the release arms 2g can now be deflected outward, whereby a movement of the slider 3 in the distal direction along the guide paths 2b is enabled. The torque from the spring 6 that acts on the gear 7 then starts to rotate the gear 7, in particular counterclockwise, in the basic insertion mechanism of the patch infusion pump 1 shown. Accordingly, the slider 3 moves in the distal direction, whereby the cannula assembly 5 and the insertion cannula assembly 4 are also shifted in the insertion direction, which leads to the introduction of insertion cannula 4a and infusion cannula 5a into the tissue of the user. FIG. 7 shows the insertion mechanism during the movement in the insertion direction.

The movement in the distal direction continues until the teeth 7c are disengaged from the toothing of the first partial crank 3b. At the same time, the cannula carrier 5b reaches the cannula guide 2d. Cannula guide 2d comprises a guide 2e, which tapers in a funnel-like manner and which thus deflects the holding arms 5d of the cannula carrier 5b inward, whereby said holding arms are brought into engagement with the cannula holder 2f. Due to the inward deflection of the holding arms 5d, the snap-in arms 5c are conversely deflected outward, whereby the engagement of the snap-in arms 5c into the cannula bridge 3d is released. Since there is still a torque attached to the gear 7, said gear in the meantime rotates counterclockwise (FIG. 8).

In FIG. 8, the insertion mechanism is shown after completed insertion of the cannulas 4a and 5a but before the retraction of the insertion cannula 4a. The gear 7 rotates between the insertion and before the retraction of the insertion cannula 4a through an angle with which the teeth 7c are not in engagement with the first partial crank 3b or the second partial crank 3c. Here, the slider remains at standstill. FIG. 8 shows the time when the teeth 7c are just in engagement with the second partial crank 3c. It should be noted that, due to the dimensioning of the first sector 7a and the circle diameter of the gear 7, the most proximal tooth of the second partial crank, half tooth 3g, is cut off, so that the movement of the gear 7 is not blocked by undesired interference with the second partial crank 3c. Moreover, it should be considered that, in the state of FIG. 8, the cannula carrier 5b is firmly connected to the cannula holder 2f, and thus the infusion cannula 5a remains in position during the retraction of the insertion cannula 4a.

In FIG. 9, the retraction movement of the slider has already started, that is to say the slider 3 moves opposite the insertion direction. The slider 3 has a changed movement direction, wherein the gear 7 always rotates in the same direction.

The end of the retraction is represented in FIG. 10. In this state, the distal arc 3h of the distal end of the guide crank 3a prevents further movement of the slider 3 in the proximal direction, in that the arc 3h comes into contact with the gear shaft 7d of the gear 7. Due to the fact that a portion of the teeth 7c is still in engagement with the toothing of the second partial crank 3c, a further rotation of the gear 7 is also no longer possible. Subsequently, the insertion mechanism has reached its final state.

An inventive embodiment of the cannula insertion mechanism is represented in FIGS. 11 to 17. The reference numerals in this embodiment were designated analogously to the above-represented basic cannula insertion mechanism of FIG. 1; the numbering was carried out in such a manner that, for example, the base 2a of the embodiment from FIG. 1 is analogous to the part 102a of the embodiment from FIG. 11. Since the function of the embodiment from FIG. 11 is also very similar to the function of the cannula insertion mechanism from FIG. 1, particular attention will be paid to the differences between the mechanisms in the following.

FIG. 11 shows an exploded representation of parts of the patch infusion device 100. FIG. 12 shows a view of the parts after the assembly in the starting state. FIG. 13a shows a view onto the arrangement from FIG. 12 in the starting state, while FIG. 14a shows the arrangement immediately after the triggering of the cannula insertion mechanism by the removal of the trigger pin 108 or release pin. FIGS. 13b and 14b show the states from FIGS. 13a and 14a, respectively, in the vertical sections M-M and N-N. FIG. 15 shows the arrangement from FIG. 12 after completed insertion of the infusion cannula 105a but before the retraction of the insertion cannula 104a. FIGS. 16 and 17 respectively show the arrangement from FIG. 12 in the final state of the cannula insertion mechanism.

As mentioned, the representation in the figures in each case do not show the entire patch infusion pump 100 but, for the sake of clarity, they show only the parts thereof that may be important to the invention.

A difference between patch infusion pump 1 and patch infusion pump 100 lies in the drive mechanism of the cannula insertion mechanism. The gear 107 is not driven directly by a torsion spring 6. The drive energy for the cannula insertion mechanism of the patch infusion pump 100 originates from the drive spring 106, which is formed as a compression spring. An end of the compression spring 106 is arranged on the compression spring counter bearing 102g, wherein the compression spring counter bearing 102g is arranged firmly on the base 102a of the housing 102 or, alternatively, it can be configured to form a single piece with the base 102a. The compression spring counter bearing 102g has a pin-shaped extension 102i that can be used as guide for the spring 106. The second end of the compression spring 106 is mounted on the toothed rod 110, more precisely on the spring bearing 110b and its pin-like extension 110e. The toothed rod 110 is mounted in such a manner that it can be shifted, in particular linearly, on the base 102a; for this purpose, the toothed rod 110 comprises the guide elements 110c, which are in particular cam-shaped guide elements (see FIG. 11), and the base 102a comprises the toothed rod guide 102k, which is in particular groove-shaped, in which the guide elements 110c are guided. FIG. 12 shows the cannula insertion mechanism in the starting state in which the compression spring 106 is tensioned (compressed). FIG. 17 shows the cannula insertion mechanism after the insertion of the infusion cannula 105a and the retraction of the insertion cannula 104a in its final state with compression spring 106 at least partially relaxed. During the relaxation movement of the spring 106, said spring has shifted the toothed rod 110 in the distal direction.

Toothed rod 110 comprises the toothing 110a, which is in engagement with the toothing of the introduction wheel 107e, so that a shifting movement of the toothed rod 110 can be converted into a rotation of the introduction wheel 107e. As shown in the figures, the introduction wheel 107e is configured as a gear. In the present embodiment, the introduction wheel 107e is firmly connected to the gear 107, or, alternatively, it is configured to form a single piece with the gear 107. Introduction wheel 107e and gear 107 are arranged coaxial to one another, wherein the gear 107 is rotationally arranged on the gear bearing 102c. In the configuration shown, the introduction wheel 107e and the gear 107 lie directly on top of each other. In alternative configurations, a spacing could also exist between the introduction wheel 107e and the gear 107, and the two parts would be firmly connected to one another, for example, via a common axle. Back to the embodiment shown: thus, if the toothed rod 110 is shifted along the toothed gear guide 102k, then, via the engagement of toothing 110a and introduction wheel 107e, the shifting brings about a rotation of the introduction wheel 107e and thus a rotation of the gear 107 relative to the base. The introduction of the drive energy for the cannula insertion mechanism thus occurs from a drive spring onto a transmission element, in this case the toothed rod 110, and from the transmission element to the introduction wheel 107e, which in turn transmits its movement to the gear 107.

Another difference between the cannula insertion mechanism of the patch infusion pump 1 and of the patch infusion pump 100 lies in the release of the cannula insertion mechanisms. The release for the cannula insertion mechanism of the patch infusion pump 100 has a clearly simpler structure than that of the patch infusion pump 1. Below, reference is made in particular to FIGS. 13a to 14b. In the starting state, the release pin 108 connects the compression spring counter bearing 102g and the toothed rod 110, in that the release pin 108 is guided through the bore 110d of the toothed rod 110 into the bore 102h of the compression spring counter bearing 102g, whereby an expansion of the compression spring 106 is blocked (see FIGS. 13a and 13b). In addition, due to the existing engagement of toothed rod 110 and introduction wheel 107e, a rotation of the gear 107 and consequently a shifting of the slider 103 are also prevented. The mechanism is released, in that the release pin 108 is pulled out of the bores, like a splint, whereby the toothed rod 110 can be shifted along the toothed rod guide 102k. The relaxing compression spring 106 brings about this shifting, which in turn results in the cannula insertion mechanism being driven. In the figures, the release pin 108 has a very simple geometric configuration. However, alternatively, the release pin 108 could also be configured as a splint that is guided through a wall of the housing 102 out of the patch infusion pump 100, enabling thereby a simple manual triggering of the cannula insertion mechanism by the user.

The release of the cannula insertion mechanism could also be configured, as in the case of the basic cannula insertion mechanism of patch infusion pump 1, without deviating from the idea of the invention.

For the further description of the function of the cannula insertion mechanism of the patch infusion pump 100, reference is made to the description of the cannula insertion mechanism of the patch infusion pump 1, which functions analogously except for the described differences or in the same way. However, it is noted again here that analogous parts bear analogous reference numerals; thus, the slider 3 of the patch infusion pump 1 corresponds to the slider 103 of the patch infusion pump 100.

Figure 18:
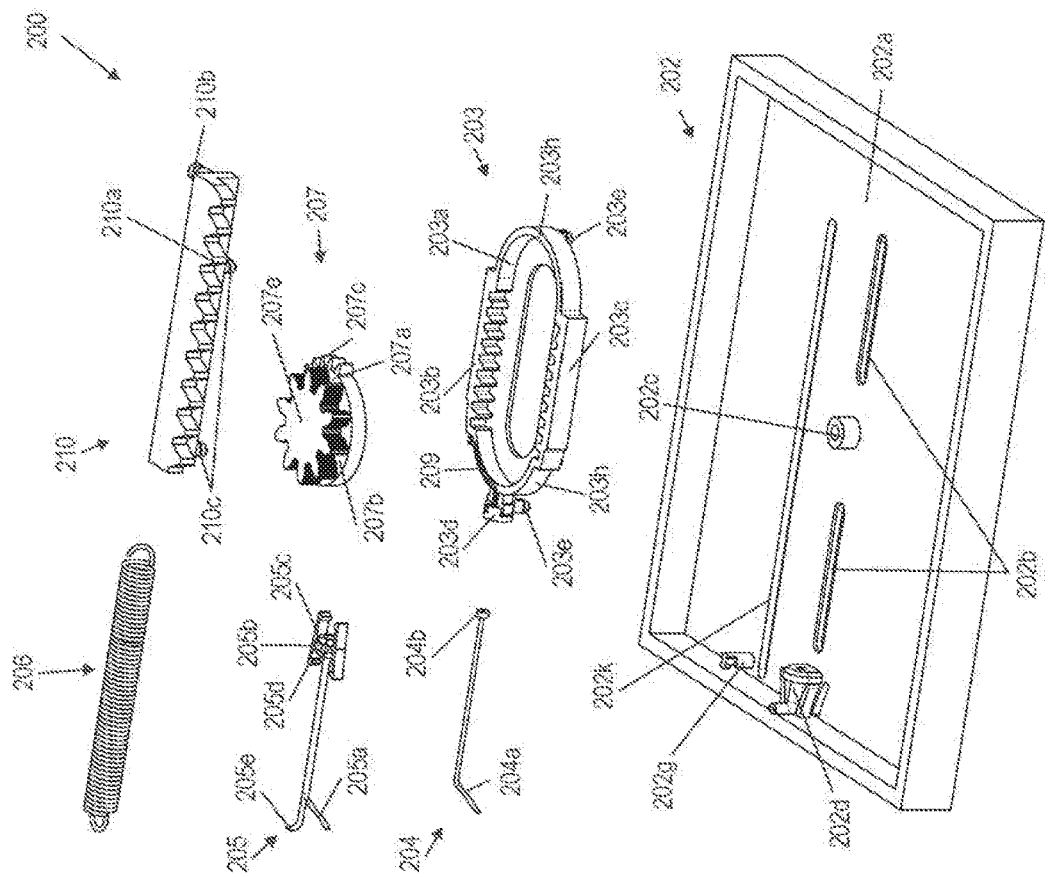
FIG. 18: Exploded representation of a cannula insertion mechanism for the patch infusion pump 200.

An inventive embodiment of the cannula insertion mechanism is represented in FIGS. 18 to 21. The reference numerals in this embodiment were designated analogously to the above-represented basic cannula insertion mechanism of FIG. 1; the numbering was carried out in such a manner that, for example, the base 2a of the configuration from FIG. 1 is analogous to the part 202a of the embodiment from FIG. 18. Since the function of the embodiment from FIG. 18 is very similar to the function of the cannula insertion mechanism from FIG. 11, particular attention will be paid to the differences between the mechanisms in the following. For the sake of clarity, no release mechanism is shown in the embodiment from FIGS. 18 to 21. However, either the release mechanism from the basic insertion mechanism (FIGS. 1 to 10) or the release mechanism from the preceding inventive embodiment (FIGS. 11 to 17) can be used. The means for implementing the release mechanism are obvious to the person skilled in the art based on the present disclosure.

Figure 21:
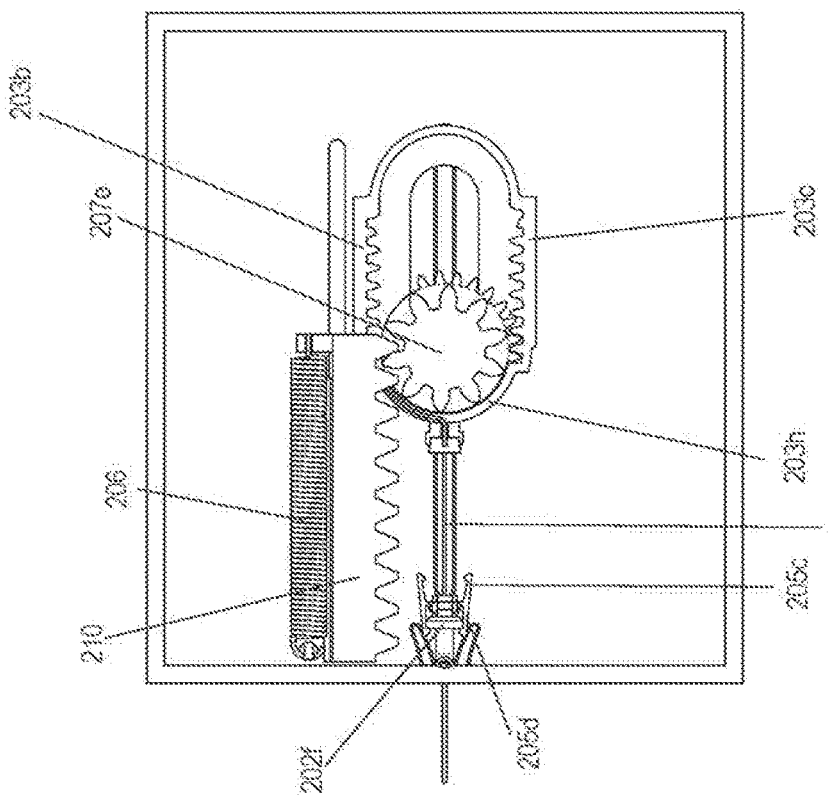
FIG. 21: View of the arrangement of the cannula insertion mechanism from FIG. 19 after completed retraction of the insertion cannula 204a (final state).
Figure 20:
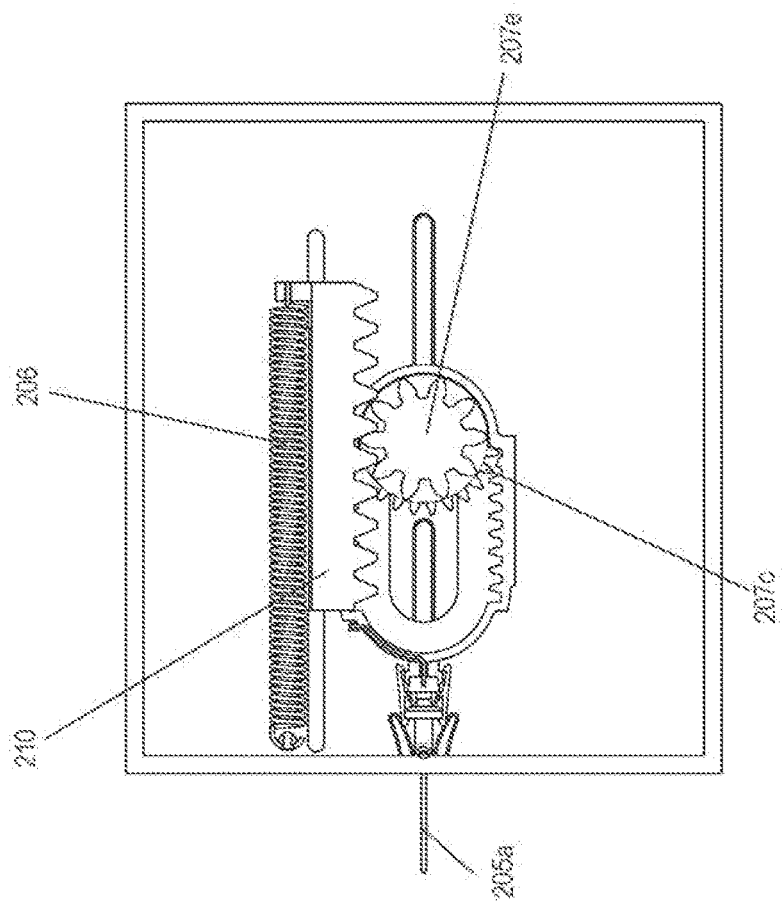

FIG. 18 shows an exploded representation of parts of the patch infusion device 200. FIG. 19 shows a view of the parts after the assembly in the starting state. FIG. 20 shows the arrangement from FIG. 19 after completed insertion of the infusion cannula 205a but before the retraction of the insertion cannula 204a. FIG. 21 shows the arrangement from FIG. 19 in the final state of the cannula insertion mechanism.

The inventive embodiment of FIGS. 18 to 21 shows a different energy source compared to the preceding embodiment. Instead of the compression spring 106, in the embodiment of FIGS. 18-21, a tension spring 206 is used in order to drive the cannula insertion mechanism. The compression spring 206 is anchored at one end to the spring bearing 202g of the base 202a and at the other end to the spring bearing 210b of the toothed rod 210. Except for this difference in terms of the drive mechanism, the embodiment from FIGS. 18 to 21 functions in the same way as the embodiment from FIGS. 11 to 17.

An inventive embodiment of the cannula insertion mechanism is represented in FIGS. 22 to 25. The reference numerals in this embodiment were designated analogously to the above-represented basic cannula insertion mechanism of FIG. 1; the numbering was carried out in such a manner that, for example, the base 2a of the configuration from FIG. 1 is analogous to the part 302a of the embodiment from FIG. 22. Since the function of the embodiment from FIG. 22 is very similar to the function of the cannula insertion mechanism from FIG. 11, particular attention will be paid to the differences between the mechanisms in the following. For the sake of clarity, no release mechanism is shown in the embodiment from FIGS. 22 to 25 either. However, either the release mechanism from the basic insertion mechanism (FIGS. 1 to 10) or the release mechanism from the inventive embodiment from FIGS. 11 to 17 can be used. The means for the implementation of the release mechanism are obvious to the person skilled in the art based on the present disclosure.

Figure 25:
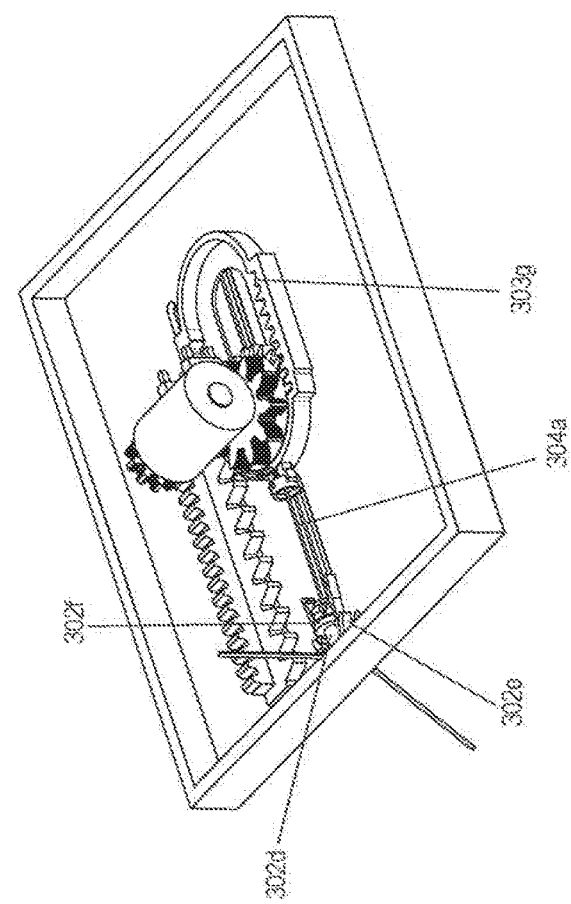
FIG. 25: View of the arrangement of the cannula insertion mechanism from FIG. 23 after completed retraction of the insertion cannula 304a (final state).
Figure 24:
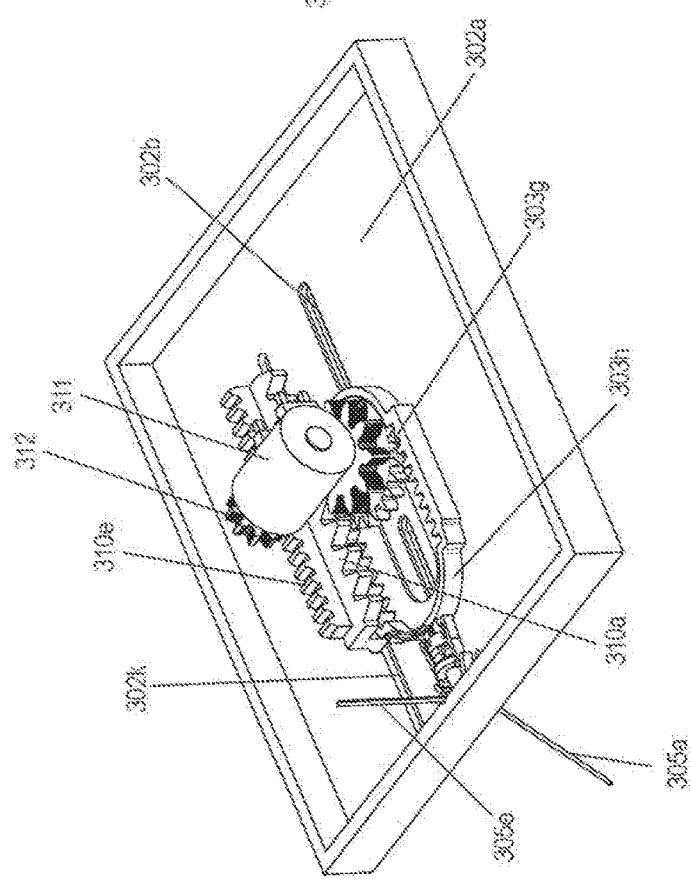

FIG. 22 shows an exploded representation of parts of the patch infusion device 300. FIG. 23 shows a view of the parts after the assembly in the starting state. FIG. 24 shows the arrangement from FIG. 23 after completed insertion of the infusion cannula 305a but before the retraction of the insertion cannula 304a. FIG. 25 shows the arrangement from FIG. 23 in the final state of the cannula insertion mechanism.

In this inventive embodiment, the energy source for the cannula insertion mechanism is not formed by a spring but instead by the electric motor 311 that sets the gear 312 into rotation, to which gear the rotation axis of the electric motor 311 is firmly connected. The motor is fastened by appropriate means to the housing 302 or to the base 302a (not shown in the figures). The gear 312 engages in the second toothing 310e, which is arranged firmly on the toothed rod 310. The toothed rod 310 has the same function as the toothed rods 110 and 210 of the previously described embodiments. A rotation of the gear 312 is converted via the second toothing 310e of the toothed rod into a shifting of the toothed rod 310 along the toothed rod guide 302k, wherein the shifting of the toothed rod 310 is converted via the toothing 310a into a rotation of the introduction wheel 307e. As is already the case in the preceding embodiments, the introduction wheel 307e is firmly connected to the toothed gear 307, which also rotates due to the rotation of the introduction wheel. As in the description of the basic cannula insertion mechanism, the rotation of the gear 307 first brings about a shifting of the slider 303 in the distal direction (insertion of the infusion cannula 305a) and subsequently a shifting of the slider in the proximal direction (retraction of the insertion cannula 304a). Except for the different drive mechanism, the cannula insertion mechanism functions in the same way as the previously described cannula insertion mechanisms of FIGS. 1 to 21.

An advantage of the embodiment of FIGS. 22 to 25 results from the fact that an electric motor is used as a drive mechanism. The electric motor 311 can be configured so that the rotation axis of the motor 311 can be rotated in the resting state only against a cogging torque, that is to say there is considerable resistance against rotation. For this purpose, the motor 311 can be formed, for example, as a DC motor with permanent magnet. Alternatively, the motor 311 can be configured as a step motor and be held actively in a position, for example. This resistance against rotation in the resting state can have the advantage that no release mechanism proper, as described above, has to be present, and the cannula insertion mechanism can be actuated via an activation of the electric motor 311. An additional advantage of the use of an electric motor can be considered to be the fact that the retraction movement of the slider 303 can be ended by stopping the motor, that is to say the retraction of the insertion cannula can be stopped, before the gear 307 comes into contact with one of the arcs 303h. In this embodiment, the arc 303h can in principle be omitted, and the starting and the stopping of the movement course of the cannula insertion mechanism as well as its starting and final position can be determined by the control of the motor.

An inventive embodiment of the cannula insertion mechanism is represented in FIGS. 26 to 29. The reference numerals in this embodiment were designated analogously to the above-represented basic cannula insertion mechanism of FIG. 1; the numbering was carried out in such a manner that, for example, the base 2a of the design from FIG. 1 is analogous to the part 402a of the embodiment from FIG. 22. Since the function of the embodiment from FIG. 26 is very similar to the function of the cannula insertion mechanism from FIG. 22, particular attention will be paid to the differences between the mechanisms in the following. For the sake of clarity, no release mechanism is shown in the embodiment from FIGS. 26 to 29 either. However, either the release mechanism from the basic insertion mechanism (FIGS. 1 to 10) or the release mechanism from the inventive embodiment from FIGS. 11 to 17 can be used. The means for the implementation of the release mechanism are obvious to the person skilled in the art based on the present disclosure.

Figure 29:
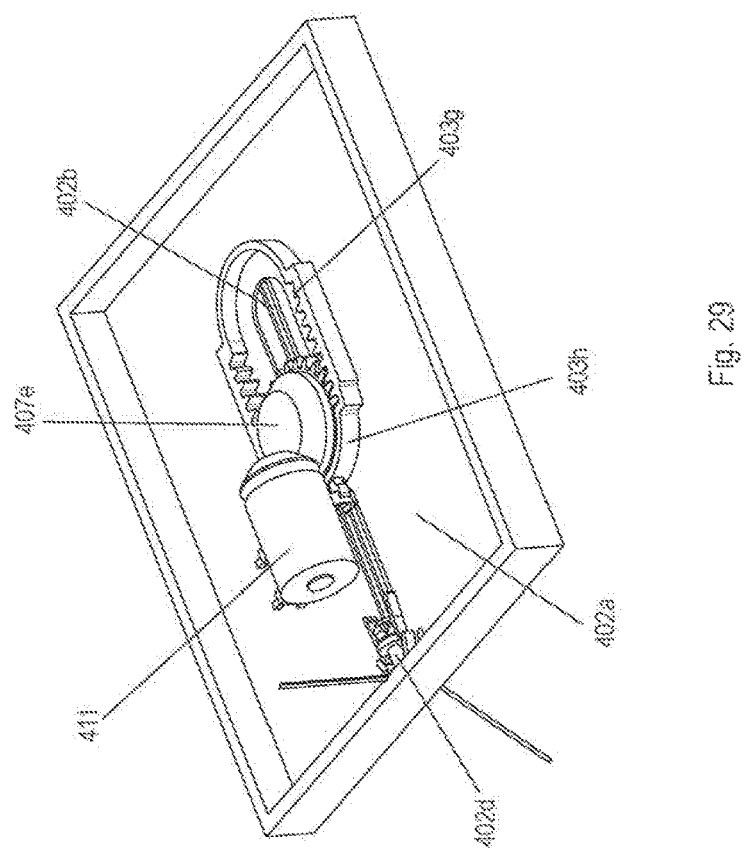
FIG. 29: View of the arrangement of the cannula insertion mechanism from FIG. 27 after completed retraction of the insertion cannula 404a (final state).
Figure 28:
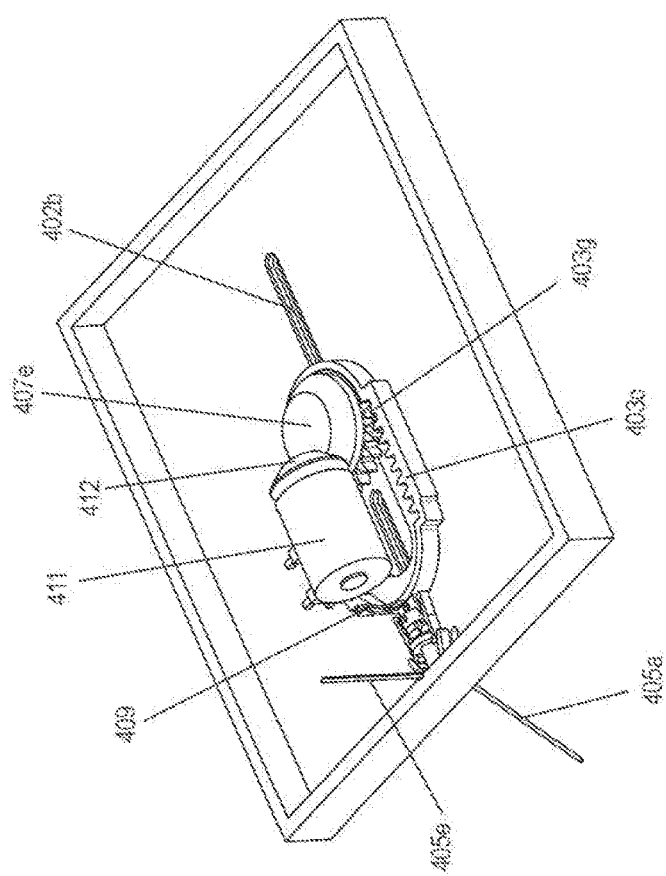

FIG. 26 shows an exploded representation of parts of the patch infusion device 400. FIG. 27 shows a view of the parts after the assembly in the starting state. FIG. 28 shows the arrangement from FIG. 27 after completed insertion of the infusion cannula 405a but before the retraction of the insertion cannula 404a. FIG. 29 shows the arrangement from FIG. 27 in the final state of the cannula insertion mechanism.

As in the previously described embodiment, the cannula insertion mechanism in this embodiment is driven by an electric motor. In contrast to patch infusion pump 300, in the case of patch infusion pump 400, the cannula insertion mechanism is not driven by a toothed rod. The motor 411 that is fastened (not shown in the figures) in the patch infusion pump 400, in particular to the housing 402 or to the base 402a, drives a bevel gear 412 that is coupled via a toothing (not shown) to the introduction wheel 407e, also configured as a bevel gear. A motor-induced rotation of the bevel gear 412 is transmitted to the introduction wheel 407e and thus to the gear 407 firmly connected to the introduction wheel 407e, which gear in turn sets the slider 403 into rotation, whereby subsequently the infusion cannula 405a together with the insertion cannula 404a is moved into the tissue of the user and subsequently the insertion cannula 404a is moved back from the tissue into the patch infusion pump 400, analogously to the above-described embodiments and configurations.

In this inventive embodiment, a toothed rod is therefore no longer needed, wherein the bevel gear 412 here takes over the function of the transmission element. Thus, the drive of the cannula insertion mechanism can be configured in a more space-saving manner than in the preceding embodiment.

In an alternative form of the patch infusion pump 400, the bevel gear wheel connection between the parts 412 and 407e is replaced by a frictional connection. In this alternative variant, the motor 411 drives a beveled friction wheel (analogous to the bevel gear 412) that is in a frictional connection with the introduction wheel 407e, which is configured alternatively also as a beveled friction wheel.

The electric motor drive mechanism of the cannula insertion mechanism of the patch infusion pump 400 otherwise has the same advantages as the electric motor drive described with regard to patch infusion pump 300.

In additional configurations, the electric motors 311 and 411 of the patch infusion pumps 300 and 400, respectively, can also be used for administering a fluid substance. This can occur in that, after the completed retraction of the insertion cannula, that is to say after the cannula insertion process has been completely terminated, the coupling between motor and introduction wheel can be released, so that the motor can continue to rotate without continuing to drive the cannula insertion mechanism. In the case of the patch infusion pump 300, this can occur, for example, in that the toothing 310a is dimensioned in such a manner that after the completion of the insertion process, the proximal end of the toothing 310 is also reached. When, subsequently, the motor 311 continues to rotate in the same direction, the gear 312 leaves the toothing 310*a* and can thus continue to rotate freely, and be coupled subsequently to an administration drive for the patch infusion pump 300. With patch infusion pump 400, the uncoupling from bevel gear 412 and introduction wheel 407*e* can occur in that the bevel gear 412 is shifted easily by the introduction wheel 407*e* along the motor axle (not shown) of the electric motor 411.

LIST OF REFERENCE NUMERALS

1 Patch infusion pump
2 Housing
2*a* Base
2*b* Guide tracks
2*c* Spring holder
2*d* Cannula guide
2*e* Funnel-like guide
2*f* Cannula holder
2*g* Release arm
2*h* Free end with tooth
2*i* Recess
2*j* Guide
3 Slider
3*a* Guide crank
3*b* First partial crank
3*c* Second partial crank
3*d* Cannula bridge
3*e* Guide elements
3*f* Tooth
3*g* Half tooth
3*h* Arc
4 Insertion cannula assembly
4*a* Insertion cannula
4*b* Insertion cannula carrier
5 Cannula assembly
5*a* Infusion cannula
5*b* Cannula carrier
5*c* Snap-in arms
5*d* Holding arms
5*e* Guide tube
6 Drive spring
7 Gear
7*a* First sector
7*b* Second sector
7*c* Teeth
7*d* Gear shaft
8 Release clamp
8*a* Spring elements
8*b* Guide arms
8*c* Bay
8*d* Free end
8*e* Blocking zone
9 Feed line
100 Patch infusion pump
102 Housing
102*a* Base
102*b* Guide tracks
102*c* Gear bearing
102*d* Cannula guide
102*e* Funnel-like guide
102*f* Cannula holder
102*g* Compression spring counter bearing
102*h* Bore
102*k* Toothed rod guide
102*l* Pin-shaped extension
103 Slider
103*a* Guide crank
103*b* First partial crank
103*c* Second partial crank
103*d* Cannula bridge
103*e* Guide elements
103*f* Tooth
103*g* Half tooth
103*h* Arc
104 Insertion cannula assembly
104*a* Insertion cannula
104*b* Insertion cannula carrier
105 Cannula assembly
105*a* Infusion cannula
105*b* Cannula carrier
105*c* Snap-in arms
105*d* Holding arms
105*e* Guide tube
106 Drive spring
107 Gear
107*a* First sector
107*b* Second sector
107*c* Teeth
107*e* Introduction wheel
108 Release pin
109 Feed line
110 Toothed rod
110*a* Toothing
110*b* Spring bearing
110*c* Guide elements
110*d* Bore
110*e* Pin-shaped extension
200 Patch infusion pump
202 Housing
202*a* Base
202*b* Guide tracks
202*c* Gear bearing
202*d* Cannula guide
202*e* Funnel-like guide
202*f* Cannula holder
202*g* Spring bearing
202*k* Toothed rod guide
203 Slider
203*a* Guide crank
203*b* First partial crank
203*c* Second partial crank
203*d* Cannula bridge
203*e* Guide elements
203*g* Half tooth
203*h* Arc
204 Insertion cannula assembly
204*a* Insertion cannula
204*b* Insertion cannula carrier
205 Cannula assembly
205*a* Infusion cannula
205*b* Cannula carrier
205*c* Snap-in arms
205*d* Holding arms
205*e* Guide tube
206 Drive spring
207 Gear
207*a* First sector
207*b* Second sector
207*c* Teeth
207*e* Introduction wheel 209 Feed line
210 Toothed rod
210a Toothing
210b Spring bearing
210c Guide elements
300 Patch infusion pump
302 Housing
302a Base
302b Guide tracks
302c Gear bearing
302d Cannula guide
302e Funnel-like guide
302f Cannula holder
302k Toothed rod guide
303 Slider
303a Guide crank
303b First partial crank
303c Second partial crank
303d Cannula bridge
303e Guide elements
303g Half tooth
303h Arc
304 Insertion cannula assembly
304a Insertion cannula
304b Insertion cannula carrier
305 Cannula assembly
305a Infusion cannula
305b Cannula carrier
305c Snap-in arms
305d Holding arms
305e Guide tube
307 Gear
307a First sector
307b Second sector
307c Teeth
307e Introduction wheel
309 Feed line
310 Toothed rod
310a Toothing
310c Guide elements
310e Second toothing
311 Electric motor
312 Gear
400 Patch infusion pump
402 Housing
402a Base
402b Guide tracks
402c Gear bearing
402d Cannula guide
402e Funnel-like guide
402f Cannula holder
403 Slider
403a Guide crank
403b First partial crank
403c Second partial crank
403d Cannula bridge
403e Guide elements
403g Holding tooth
403h Arc
404 Insertion cannula assembly
404a Insertion cannula
404b Insertion cannula carrier
405 Cannula assembly
405a Infusion cannula
405b Cannula carrier
405c Snap-in arms
405d Holding arms
405e Guide tube
407 Gear
407a First sector
407b Second sector
407c Teeth
407e Introduction wheel
409 Feed line
411 Electric motor
412 Bevel gear

What is claimed is:

1. A drive mechanism for an insertion mechanism for an administration device, comprising:
a flat or curved base;
a guide track formed in or on the base, wherein the guide track defines a proximal end and a distal end and in between a straight line or a curve;
a slider rotationally fixed relative to the base and configured to be slid along or in the guide track between a proximal slider end position and a distal slider end position;
a drive wheel rotatably mounted on the base;
a drive track coupled to the slider, the drive track comprising a plurality of drive sections, wherein a first drive section of the plurality of drive sections and a second drive section of the plurality of drive sections lie opposite each other or extend parallel to the straight line or to the curve of the guide track; and
an energy source configured to cause the drive wheel to rotate relative to the base and the slider,
wherein, upon rotation of the drive wheel, the slider is shifted from the proximal slider end position by a positive-connection or non-positive connection engagement of the drive wheel in the first drive section of the plurality of drive sections, along or in the guide track in a distal direction, and at a distal end of the first drive section of the plurality of drive sections the positive-connection or non-positive connection engagement of the drive wheel switches from the first drive section of the plurality of drive sections to the second drive section of the plurality of drive sections by a further rotation of the drive wheel, and the slider is shifted along or in the guide track in a proximal direction, and
wherein the energy source can be coupled to the drive wheel by a one-piece or a multi-piece transmission element and an introduction wheel, said introduction wheel being connected in a rotationally fixed manner to the drive wheel, and said transmission element being arranged such that it can be shifted or rotated relative to the base.

2. The drive mechanism of claim 1, wherein the transmission element comprises a toothed rod, and wherein the introduction wheel is a gear comprising teeth configured to engage with a toothing of the toothed rod such that the transmission element can be shifted on the base by a toothed engagement between the teeth of the gear and the toothing of the toothed rod.

3. The drive mechanism of claim 2, wherein the base comprises a linear toothed rod guide in the form of a groove, and wherein the gear comprises at least one guide element via which the toothed rod is connected to the base, and wherein the toothed rod can be shifted along the toothed rod guide.

4. The drive mechanism of claim 3, wherein the energy source is a tension or compression spring, wherein a first end of the tension or compression spring is fixedly connected to the base and a second end fixedly connected to the toothed rod, and wherein the tension or compression spring is pretensioned or can be pretensioned for the driving of the drive mechanism for the insertion mechanism of the administration device, and wherein, by a release of the pretensioned tension or compression spring, a force acts on the toothed rod, which sets said toothed rod in motion along the toothed rod guide and wherein subsequently the introduction and drive wheels are set into rotation.

5. The drive mechanism of claim 2, wherein the drive mechanism comprises a release device, wherein the release device comprises:
   a holding element fixedly connected to the base;
   an additional holding element arranged on the toothed rod; and
   a connecting element with which the holding element and the additional holding element can be detachably connected to one another,
   wherein, when the holding element and the additional holding element are connected to one another via the connecting element, the toothed rod is held fixed relative to the base.

6. The drive mechanism of claim 5, wherein the holding element and the additional holding element are configured as bores, and the connecting element is configured as a pin or a splint that can be introduced into the bores such that the toothed rod can be fixed relative to the base.

7. The drive mechanism of claim 2, wherein the toothed rod comprises a first toothing and a second toothing, wherein the first toothing can be brought into engagement with the introduction wheel formed as a gear, and wherein the energy source can be coupled via the second toothing to the toothed rod.

8. The drive mechanism of claim 7, wherein the energy source comprises an electric motor with an electric motor drive axle that can be set into rotation by the electric motor directly or via a transmission, and wherein, on the electric motor drive axle, a gear is coaxially and fixedly arranged, which can be brought in engagement with the second toothing of the toothed rod.

9. The drive mechanism of claim 1, wherein the introduction wheel is configured as a first bevel gear wheel and the transmission element is configured as a second bevel gear wheel, wherein the first bevel gear wheel and the second bevel gear wheel are in engagement with one another, such that a rotation of the second bevel gear wheel brings about a rotation of the first bevel gear wheel, and wherein the rotation axes of the first and the second bevel gear wheel are at an angle of approximately 90° relative to one another.

10. The drive mechanism of claim 9, wherein the second bevel gear wheel can be set into rotation by an electric drive or a spring.

11. The drive mechanism of claim 1, wherein the slider comprises a feed line with a lumen and is guided in or on the slider, through which a substance to be administered can be received.

12. The drive mechanism of claim 11, wherein, on a distal end of the slider, a cannula bridge is arranged, at which the feed line ends and on which a proximal end of an insertion cannula with a lumen is arranged, wherein the lumen of the feed line and the lumen of the insertion cannula are connected to one another such that the substance to be administered can be led from the feed line into the insertion cannula, and wherein the insertion cannula is shiftable along the slider in the distal direction and in the proximal direction.

13. A cannula insertion mechanism for a patch device, comprising
   a drive mechanism, comprising
      a base;
      a guide track formed in or on the base;
      a slider rotationally fixed relative to the base and configured to be slid along or in the guide track between a proximal slider end position and a distal slider end position, wherein the slider comprises a feed line with a lumen and is guided in or on the slider, through which a substance to be administered can be received, wherein, on a distal end of the slider, a cannula bridge is arranged, at which the feed line ends and on which a proximal end of an insertion cannula with a lumen is arranged, wherein the lumen of the feed line and the lumen of the insertion cannula are connected to one another such that the substance to be administered can be led from the feed line into the insertion cannula, and wherein the insertion cannula is shiftable along the slider in the distal direction and in the proximal direction;
      a drive wheel rotatably mounted on the base;
      a drive track coupled to the slider, the drive track comprising a plurality of drive sections, wherein a first drive section of the plurality of drive sections and a second drive section of the plurality of drive sections lie opposite each other or extend parallel to the guide track;
      an energy source, by means of which the drive wheel can be set into rotation relative to the base and the slider,
      wherein, upon rotation of the drive wheel, the slider is shifted from the proximal slider end position in the first drive section of the plurality of drive sections, along or in the guide track in a distal direction, and at a distal end of the first drive section of the plurality of drive sections, the drive wheel switches from the first drive section of the plurality of drive sections to the second drive section of the plurality of drive sections by a further rotation of the drive wheel, and the slider is shifted along or in the guide track in a proximal direction, and
      wherein the energy source can be coupled to the drive wheel by a one-piece or a multi-piece transmission element and an introduction wheel, wherein the introduction wheel is connected in a rotationally fixed manner to the drive wheel, and wherein the transmission element is arranged such that said transmission element can be shifted or rotated relative to the base,
   an infusion cannula with a distal and a proximal end, through which the insertion cannula can be guided, and
   wherein, on the proximal end of the infusion cannula, a cannula carrier is fixedly coupled, wherein, on the cannula carrier, a connecting means is arranged, via which the cannula carrier can be detachably connected to the cannula bridge when the insertion cannula is guided through the infusion cannula until the cannula carrier is in contact with the cannula bridge.

14. The cannula insertion mechanism of claim 13, wherein the insertion mechanism is configured as a patch device.

15. The cannula insertion mechanism of claim 14, wherein the patch device is a patch pump or a patch injection device.

16. A drive mechanism for an insertion mechanism for an administration device, comprising:
   a base;
   a guide track formed in or on the base;
   a slider rotationally fixed relative to the base, wherein the slider is configured to be slid along or in the guide track between a proximal slider end position and a distal slider end position;
   a drive wheel rotatably mounted on the base;
   a drive track coupled to the slider, the drive track comprising a plurality of drive sections, wherein a first drive section of the plurality of drive sections and a second drive section of the plurality of drive sections lie opposite each other or extend parallel to the guide track; and
   an energy source configured to cause the drive wheel to rotate relative to the base and the slider,
   wherein, upon rotation of the drive wheel, the slider is shifted from the proximal slider end position in the first drive section of the plurality of drive sections, along or in the guide track in a distal direction, and at a distal end of the first drive section of the plurality of drive sections, the drive wheel switches from the first drive section of the plurality of drive sections to the second drive section of the plurality of drive sections by a further rotation of the drive wheel, and the slider is shifted along or in the guide track in a proximal direction,
   characterized in that the energy source can be coupled to the drive wheel by a transmission element and an introduction wheel, wherein the introduction wheel is connected in a rotationally fixed manner to the drive wheel, and wherein the transmission element is arranged such that said transmission element can be shifted or rotated relative to the base.

17. The drive mechanism of claim 16, wherein the transmission element comprises a toothed rod, and wherein the introduction wheel is configured as a gear comprising teeth for engaging with a toothing of the toothed rod such that the transmission element can be shifted on the base by a toothed engagement between the teeth of the gear and the toothing of the toothed rod.

18. The drive mechanism of claim 17, wherein the energy source is a tension or compression spring, wherein a first end of the tension or compression spring is connected to the base and a second end connected to the toothed rod, and wherein the tension or compression spring is pretensioned or can be pretensioned for the driving of the drive mechanism for the insertion mechanism of the administration device, and wherein, by a release of the pretensioned tension or compression spring, a force acts on the toothed rod, which sets said toothed rod in motion, and wherein the introduction wheel and drive wheel are set into rotation.

19. The drive mechanism of claim 16, wherein the slider comprises a feed line with a lumen and is guided in or on the slider, through which a substance to be administered can be received.

* * * * *

UNITED STATES PATENT AND TRADEMARK OFFICE
CERTIFICATE OF CORRECTION

PATENT NO. : 11,197,954 B2
APPLICATION NO. : 16/516051
DATED : December 14, 2021
INVENTOR(S) : Seline Staub and Ursina Streit Page 1 of 1

It is certified that error appears in the above-identified patent and that said Letters Patent is hereby corrected as shown below:

In the Claims

In Column 22, Line 49, Claim 1 delete ""it"" and replace with -- said transmission element --

Signed and Sealed this
Eighth Day of March, 2022

Drew Hirshfeld
*Performing the Functions and Duties of the*
*Under Secretary of Commerce for Intellectual Property and*
*Director of the United States Patent and Trademark Office*